US011982726B2

(12) United States Patent
Nayak et al.

(10) Patent No.: US 11,982,726 B2
(45) Date of Patent: May 14, 2024

(54) METHOD FOR JOINT ARTERIAL INPUT FUNCTION AND TRACER KINETIC PARAMETER ESTIMATION IN ACCELERATED DCE-MRI USING A MODEL CONSISTENCY CONSTRAINT

(71) Applicant: UNIVERSITY OF SOUTHERN CALIFORNIA, Los Angeles, CA (US)

(72) Inventors: Krishna S. Nayak, Long Beach, CA (US); Yannick Bliesener, Los Angeles, CA (US); Yi Guo, San Francisco, CA (US); Yinghua Zhu, Lexington, MA (US); Sajan Goud Lingala, Los Angeles, CA (US); Robert Marc Lebel, Calgary (CA)

(73) Assignee: University of Southern California, Los Angeles, CA (US)

( * ) Notice: Subject to any disclaimer, the term of this patent is extended or adjusted under 35 U.S.C. 154(b) by 960 days.

(21) Appl. No.: 16/384,795

(22) Filed: Apr. 15, 2019

(65) Prior Publication Data
US 2019/0317171 A1    Oct. 17, 2019

Related U.S. Application Data

(60) Provisional application No. 62/657,452, filed on Apr. 13, 2018.

(51) Int. Cl.
*G01R 33/563* (2006.01)
*A61B 5/055* (2006.01)
(Continued)

(52) U.S. Cl.
CPC ........ *G01R 33/56308* (2013.01); *A61B 5/055* (2013.01); *G01R 33/5601* (2013.01); (Continued)

(58) Field of Classification Search
CPC .. A61B 5/055; A61B 5/0263; G01R 33/5601; G01R 33/56308; G01R 33/56366;
(Continued)

(56) References Cited

U.S. PATENT DOCUMENTS

2002/0026110 A1* 2/2002 Parris ................. A61B 5/14532
600/347
2012/0033869 A1* 2/2012 Carlsen ............ G01R 33/56366
382/131

OTHER PUBLICATIONS

Giovanni A. Buonaccorsi et al. "Tracer Kinetic Model-Driven Registration for Dynamic Contrast-Enhanced MRI Time-Series Data", Magnetic Resonance in Medicine 58:1010-1019 (2007) accepted Aug. 1, 2007 (Year: 2007).*

(Continued)

*Primary Examiner* — Shahdeep Mohammed
*Assistant Examiner* — Fikirte (Fiki) T Ashine
(74) *Attorney, Agent, or Firm* — Brooks Kushman P.C.

(57) ABSTRACT

Tracer kinetic models are utilized as temporal constraints for highly under-sampled reconstruction of DCE-MRI data. In one embodiment, a method for improving dynamic contrast enhanced imaging. The method includes steps of administering a magnetic resonance contrast agent to a subject and then collecting magnetic resonance contrast agent from the subject. A tracer kinetic model (i.e. eTofts or Patlak) is selected to be applied to the magnetic resonance imaging data. The tracer kinetic model is applied to the magnetic resonance imaging data. Tracer kinetic maps and dynamic images are simultaneously reconstructed and a consistency constraint is applied. The proposed method allows for easy use of different tracer kinetic models in the formulation and estimation of patient-specific arterial input functions jointly with tracer kinetic maps.

34 Claims, 15 Drawing Sheets

(51) Int. Cl.
*G01R 33/56* (2006.01)
*A61K 49/10* (2006.01)
*G01R 33/28* (2006.01)
*G01R 33/385* (2006.01)

(52) U.S. Cl.
CPC .......... *A61K 49/103* (2013.01); *G01R 33/281* (2013.01); *G01R 33/385* (2013.01); *G06T 2207/10088* (2013.01)

(58) Field of Classification Search
CPC ................ G01R 33/281; G01R 33/385; G01R 33/5611; A61K 49/103; G06T 2207/10088
See application file for complete search history.

(56) References Cited

OTHER PUBLICATIONS

Tong San Koh et al., "Fundamentals of Tracer Kinetics for Dynamic Contrast-Enhanced MRI" Journal of Magnetic Resonance Imaging 34:1262-1276 (2011) Jul. 19, 2011 (Year: 2011) (Year: 2011).*

Bernd J. Pichler et al., "Positron Emission Tomography/Magnetic Resonance Imaging: The Next Generation of Multimodality Imaging", Nuclear Medicine, Elsevier , published 2008. (Year: 2008).*

Giovanni A. Buonaccorsi et al. (hereafter Buonaccorsi)"Tracer Kinetic Model-Driven Registration for Dynamic Contrast-Enhanced MRI Time-Series Data", Magnetic Resonance in Medicine 58:1010-1019 pub. on Aug. 1, 2007. (2007) (Year: 2007).*

Tong San Koh et al. (hereafter Koh) "Fundamentals of Tracer Kinetics for Dynamic Contrast-Enhanced MRI" Journal of Magnetic Resonance Imaging 34:1262-1276 published on Jul. 19, 2011. (Year: 2011).*

Pichler et al., (hereafter Pichler), "Positron Emission Tomography/ Magnetic Resonance Imaging: The Next Generation of Multimodality Imaging", Nuclear Medicine, Elsevier , published 2008. (Year: 2008).*

Giovanni et al., "Tracer Kinetic Model-Driven Registration for Dynamic Contrast-Enhanced MRI Time-Series Data", Magnetic Resonance in Medicine 58:1010-1019 (Year: 2007).*

Tong San Koh et al., "Fundamentals of Tracer Kinetics for Dynamic Contrast-Enhanced MRI" Journal of Magnetic Resonance Imaging 34:1262-1276 (Year: 2011).*

Guo, Y. et al., "Joint Arterial Input Function and Tracker Kinetic Parameter Estimation from Undersampled Dynamic Contrast-Enhanced MRI Using a Model Consistency Constraint," Magnetic Resonance in Medicine, 2017, 12 pgs.

* cited by examiner

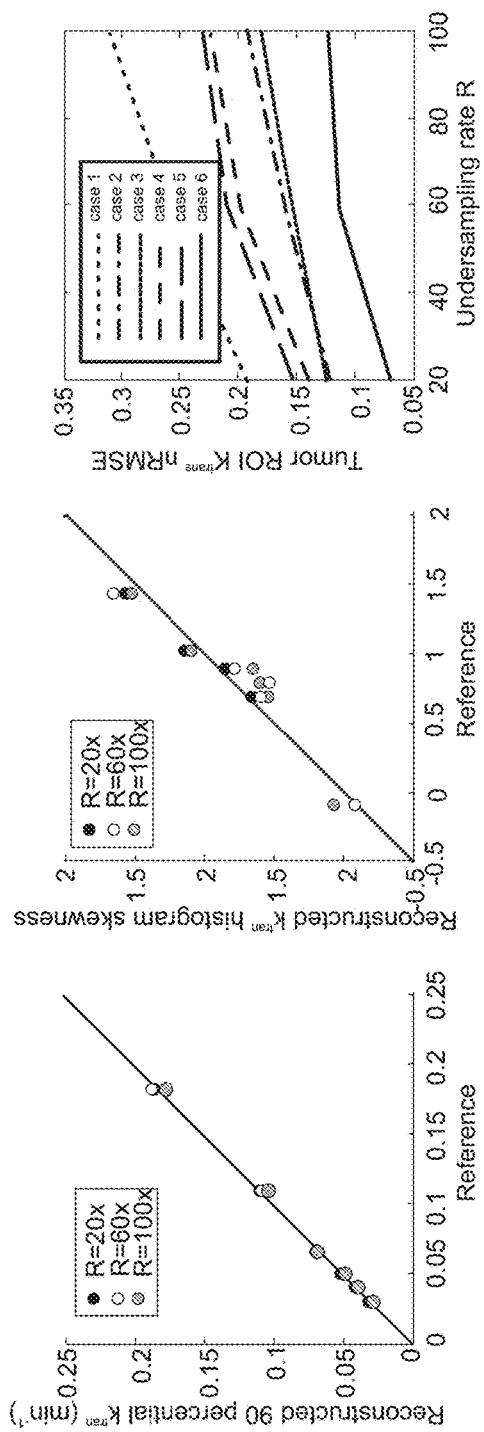
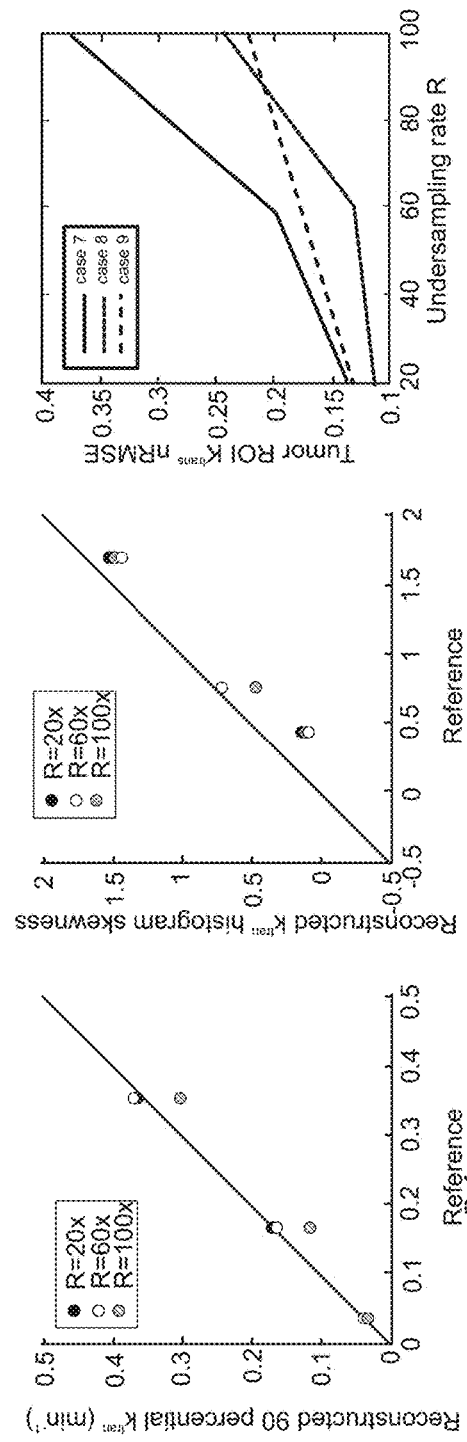
Fig. 8A Fig. 8B Fig. 8C Fig. 8D Fig. 8E Fig. 8F

METHOD FOR JOINT ARTERIAL INPUT FUNCTION AND TRACER KINETIC PARAMETER ESTIMATION IN ACCELERATED DCE-MRI USING A MODEL CONSISTENCY CONSTRAINT

CROSS-REFERENCE TO RELATED APPLICATIONS

This application claims the benefit of U.S. provisional application Ser. No. 62/657,452 filed Apr. 13, 2018, the disclosure of which is hereby incorporated in its entirety by reference herein.

TECHNICAL FIELD

In at least one embodiment, the present invention relates to methods for improving magnetic resonance imaging.

BACKGROUND

Dynamic Contrast Enhanced Magnetic Resonance Imaging (DCE-MRI) is a time resolved methodology of MRI, which involves intravenous administration of a paramagnetic contrast agent and continuous acquisition of images to track the passage of the contrast through a volume of interest. DCE-MRI is used most often to evaluate cancer (tumor vascularity), but can also be applied to other diseases. DCE-MRI is a powerful technique for probing sub-voxel vascular properties of tissue including fractional plasma volume, fractional extra-cellular-extravascular volume, and clinically important transfer constants. DCE-MRI involves capturing a series of images before, during, and after administration of a $T_1$-shortening contrast agent.

Tracer-kinetic (TK) modeling of the enhancement kinetics of the contrast agent enables quantification of TK parameters such as $K^{trans}$: a volume transfer coefficient across the capillary endothelium, and fractional volumes such as $V_e$ (fractional volume of the extravascular extracellular space), and $v_p$ (fractional plasma volume). These parameters provide a means as functional biomarkers in diagnosis and treatment planning of cancer in several body parts including the brain, breast, liver, and prostate. In the brain, DCE-MRI characterizes the blood-brain barrier leakiness, which has important implications as a potential early biomarker in the evaluation of neuro-degenerative diseases such as Alzheimer's disease, multiple sclerosis, and vascular dementia.

DCE-MRI is a 4-dimensional (x, y, z, time) imaging task, and is challenged by slow MRI acquisition speed. Tracer-kinetic (TK) parameter maps are then computed from the dynamic images, and provide information for diagnosis and monitoring treatment response (1-3). DCE-MRI is used throughout the body, most commonly in the prostate, breast, liver, and brain. In the brain, DCE-MRI has shown value in the assessment of brain tumor, multiple sclerosis, and Alzheimer disease (4-6).

With conventional Nyquist sampling, DCE-MRI is often unable to simultaneously provide adequate spatiotemporal resolution and spatial coverage. A typical brain DCE-MRI provides 5-s temporal resolution, which is a minimum requirement for accurate TK modeling (7,8). Using Cartesian sampling at the Nyquist rate, only 5-10 slices are achievable. This is typically inadequate in large glioblastoma cases and cases with scattered metastatic disease that may be spread throughout the brain (9). It is possible to coarsen spatial resolution to achieve greater spatial coverage, but this compromises the ability to evaluate the narrow (1-2 mm) enhancing margin of glioblastomas and the ability to evaluate small lesions.

Thus, techniques involving under-sampling and constrained reconstruction have been proposed to simultaneously provide high spatial resolution and whole-brain coverage. Early work used compressed sensing and parallel imaging to reconstruct dynamic images from under-sampled k,t-space data (10-12). Standard TK modeling software was then used to generate high-resolution whole-brain TK maps based on the reconstructed images (9,13). A more recent proposed approach was to enforce the TK model and directly estimate TK parameters from under-sampled k,t-space data (14). Similar model-based reconstruction approaches have been used for MRI relaxometry (15,16), PET kinetic parameter estimation (17,18), and recently, DCE-MRI kinetic parameter estimation (14,19-21). Compared with conventional compressed sensing techniques that reconstruct dynamic images first, the model-based approach provides superior results and allows higher under-sampling rates (14,21). Direct kinetic parameter estimation makes the most efficient use of acquired information; however, it is sensitive to inaccuracy of the forward model. Two major issues with this are variations in the arterial input function (22) and prior knowledge of the appropriate TK model (23-25).

In conventional DCE-MRI, images are reconstructed for each time point. Patient-specific arterial input functions (AIF) can be identified from vessel voxels using either manual region of interest (ROI) selection or automatic cluster-based ROI selection (26). Some centers use a fixed population-averaged AIF (27), an institutionally derived population AIF, or a delay and dispersion-corrected version of these (9). The use of a patient-specific AIF (pat-AIF) is generally preferred because it is known to provide more accurate TK mapping (22). The estimation of pat-AIF from under-sampled data is extremely challenging due to under-sampling artifacts. Current model-based TK reconstruction approaches rely on the use of a population-averaged AIF (pop-AIF) (14,21). This is considered a major limitation of these approaches because the use of a pop-AIF can lead to significant errors in the resulting TK maps (22).

Accordingly, there is a need for improved methods implementing dynamic contrast enhanced magnetic resonance imaging.

SUMMARY

The present invention solves one or more problems of the prior art by providing in at least one embodiment, a flexible framework for direct model-based reconstruction of accelerated DCE-MRI.

In at least one aspect, the present invention involves a DCE-MRI reconstruction approach that allows for integration of different TK models and/or different TK solvers as well as joint estimation of the patient-specific AIF and TK parameter maps. The performance of the present invention was evaluated using simulated DCE-MRI data from a physiologically realistic digital reference object (DRO) and in vivo DCE-MRI data from brain tumor patients. The application of the present invention was tested on prospectively under-sampled high-resolution whole-brain DCE-MRI data.

In another aspect, the present invention provides simultaneous reconstruction of TK maps and dynamic images, where TK model consistency is applied as a penalized reconstruction constraint and the pat-AIF can be iteratively estimated from the dynamic images. This approach is inspired by recent studies of accelerated quantitative MR relaxometry (28,29), where physical or physiological model consistency was applied as a penalized reconstruction constraint (not strictly enforced). This consistency constraint allowed for the data fit to deviate from the model, which made the scheme robust to scenarios with model inconsistencies (e.g., motion). For DCE-MRI, TK model is applied as a consistency constraint with a regularization parameter that balances the tradeoff between data consistency and model consistency.

In another aspect, a method for improving dynamic contrast enhanced imaging for joint arterial input function and tracer kinetic parameter estimation is provided. The method includes steps of administering a contrast agent (e.g., a magnetic resonance contrast agent) to a subject and then collecting imaging data (e.g., magnetic resonance imaging data) from the subject for a tissue or organ. A tracer kinetic model (e.g., eTofts or Patlak) is selected to be applied to the magnetic resonance imaging data. The tracer kinetic model is defined by a plurality of tracer kinetic parameters. The tracer kinetic model is applied to the magnetic resonance imaging data to estimate the tracer kinetic parameter map. Tracer kinetic maps and dynamic images are reconstructed by alternating between the reconstruction for tracer kinetic maps and dynamic images until data and model consistency are met simultaneously. In a refinement, the tracer kinetic model is automatically selected from estimated contrast concentration versus time images and estimated patient specific AIF.

In another aspect, a method for improving dynamic contrast enhanced imaging for joint arterial input function and tracer kinetic parameter estimation is provided. The method includes steps of administering a contrast agent (e.g., a magnetic resonance contrast agent) to a subject; collecting imaging data (e.g., a magnetic resonance imaging data) from the subject for a tissue or organ; selecting a tracer kinetic model to be applied to the imaging data, the tracer kinetic model being defined by a plurality of tracer kinetic parameters; and reconstructing dynamic images from the imaging data as reconstructed dynamic images. The method further includes a step of applying the tracer kinetic model to the reconstructed dynamic images to estimate tracer kinetic parameter maps as estimated tracer kinetic parameter maps. Reconstructed dynamic images and estimated tracer kinetic parameter maps are jointly forced to be consistent with the measurement data and the selected tracer kinetic model. Characteristically, this simultaneous consistency is enforce in form of a weighted sum of a data consistency component and a model consistency component. Finally, the steps of reconstructing dynamic images and applying the tracer kinetic model are alternately performed until converging on a set of dynamic images and tracer kinetic parameter maps.

In still another aspect, a system for improving dynamic contrast enhanced imaging for joint arterial input function and tracer kinetic parameter estimation is provided. The system is a magnetic resonance imaging system that generates magnetic resonance imaging data from a subject for a tissue or organ and a programmable computer. The programmable computer is operable to execute steps of: collecting the magnetic resonance imaging data from the subject and reconstructing dynamic images from the magnetic resonance imaging data as reconstructed dynamic images. The programmable computer is further operable to apply a tracer kinetic model to the reconstructed dynamic images to estimated tracer kinetic parameter maps. The computer is operable to apply a consistency constraint to the reconstructed dynamic images and the estimated tracer kinetic parameter maps. Characteristically, the consistency constraint includes a weighted sum of a data consistency component and a model consistency component; The programmable computer is further operable to alternately perform the steps of reconstructing dynamic images and applying the tracer kinetic model until converging on a set of dynamic images and tracer kinetic parameter maps.

BRIEF DESCRIPTION OF THE DRAWINGS

FIG. 8A. Quantitative evaluation for the Patlak model reconstruction on retrospective under-sampled in vivo cases.

FIG. 8B. Plot of $K^{trans}$ skewness against the reference histogram skewness for the Patlak model.

FIG. 8C. nRMSE values based on under-sampling rates for the Patlak model.

FIG. 8D. Quantitative evaluation of the eTofts reconstruction on retrospective under-sampled in vivo cases.

FIG. 8E. Plot of $K^{trans}$ skewness against the reference histogram skewness for the eTofts model.

FIG. 8F. nRMSE values based on under-sampling rates for the eTofts model.

DETAILED DESCRIPTION

Figure 1A:
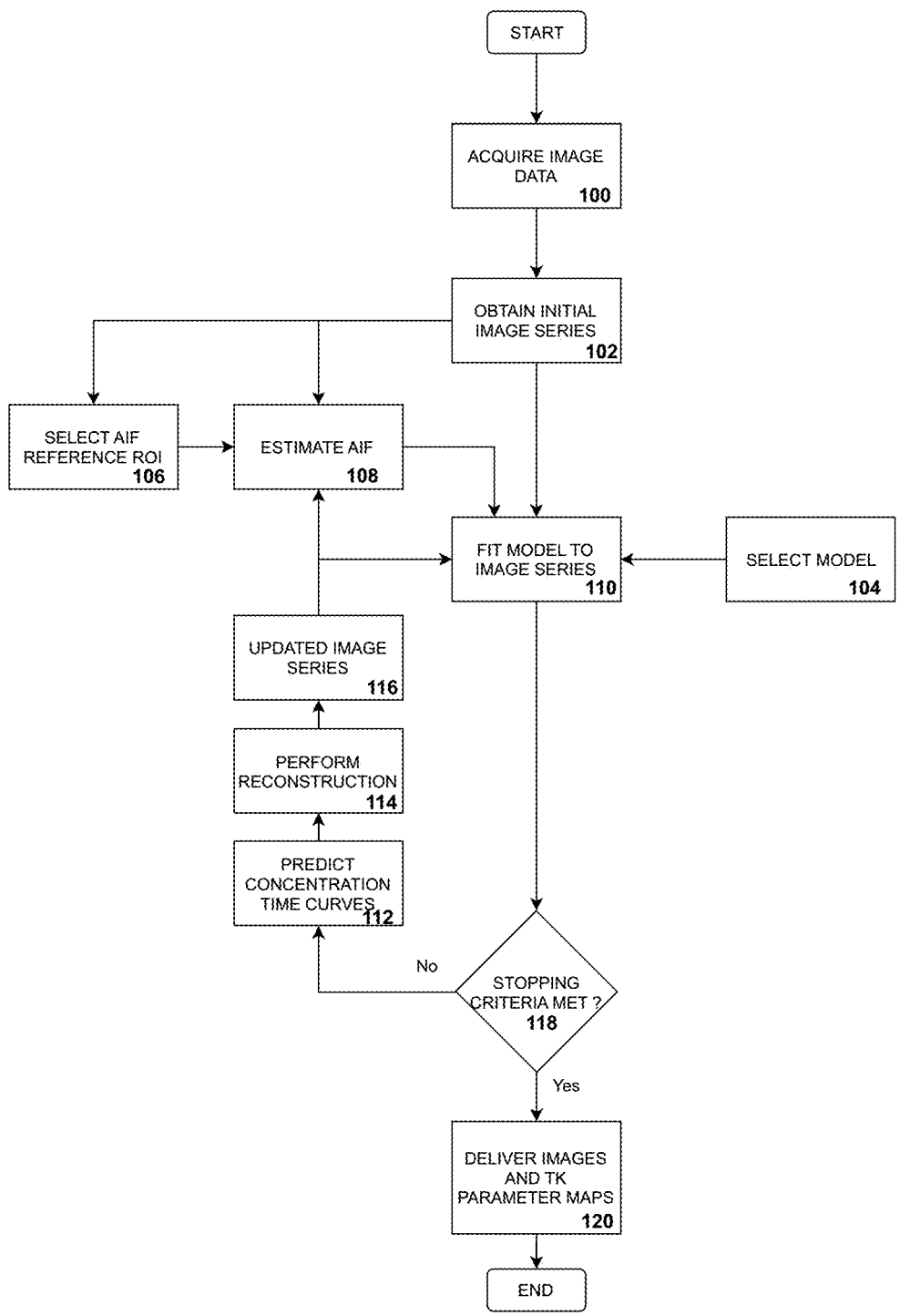
FIG. 1A. Flowchart applying tracer kinetic parameter estimation with a preselected model.

Reference will now be made in detail to presently preferred compositions, embodiments and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

When a computer is described as performing an action or method step, it is understood that the computing devices is operable to perform the action or method step typically by executing one or more line of source code. The actions or method steps can be encoded onto non-transitory memory (e.g., hard drives, optical drive, flash drives, and the like).

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Abbreviations:
"AIF" means arterial input function.
"DCE-MRI" means dynamic contrast enhanced magnetic resonance imaging.
"ETK" means extended Tofts-Kety.
"MRI" means magnetic resonance imaging.
"TK" means tracer-kinetic.
"ROI" region of interest.

In at least one embodiment, a method for improving dynamic contrast enhanced imaging is provided. The method includes steps of administering a contrast agent (e.g., a magnetic resonance) to a subject and then collecting imaging data (e.g., a magnetic resonance imaging data) from the subject for a tissue or organ. A tracer kinetic model (e.g., ETK or Patlak) is selected to be applied to the imaging data. In a refinement, the tracer kinetic model is selected from a library of tracer kinetic models such that one or more tracer kinetic model from the library are applied to find an optimal tracer kinetic model. The tracer kinetic model is defined by a plurality of tracer kinetic parameters. The tracer kinetic model is applied to the imaging data to estimate the tracer kinetic parameter map. Dynamic images and tracer kinetic parameter maps are reconstructed from the imaging data. A consistency constraint is applied to dynamic images and estimated tracer kinetic parameter maps. Reconstructed dynamic images and estimated tracer kinetic parameter maps are jointly forced to be consistent with the measurement data and the selected tracer kinetic model. Characteristically, this simultaneous consistency is enforced in form of a weighted sum of a data consistency component and a model consistency component. The tracer kinetic model is applied to the reconstructed dynamic images to estimate tracer kinetic parameter maps. The steps of reconstructing dynamic images with consistency constraint and of applying the tracer kinetic model are alternatively performed (e.g. in an alternating fashion) until converging on a set of dynamic images and tracer kinetic parameter maps. In a refinement, the consistency constraint is iteratively enforced to the dynamic images first followed by the tracer kinetic maps. In another refinement, the tracer kinetic model is selected automatically from during estimation of contrast concentration versus time images and patient-specific AIF from under-sampled data.

The methods of the present embodiment are advantageously used for determining an arterial input function (AIF) sometimes referred to as vascular input function (VIP) from the imaging data (e.g., magnetic resonance imaging data or other dynamic contrast imaging techniques such as positron dynamic contrast positron emission tomography data), wherein the arterial input function includes a time variation of the contrast agent concentration at one or more predetermined locations in an artery of the subject. The arterial input function is taken as surrogate for the vascular input function. Typically, the arterial input function is determined as a function of time. In other variation, the tissue or organ to which the method is applied can be selected from the group consisting of brain, breast, prostate, liver, kidney, lung, heart, thyroid, pancreas, spleen, intestine, uterus, ovary, limbs, spleen, spine,bones, and eyes.

Figure 1B:
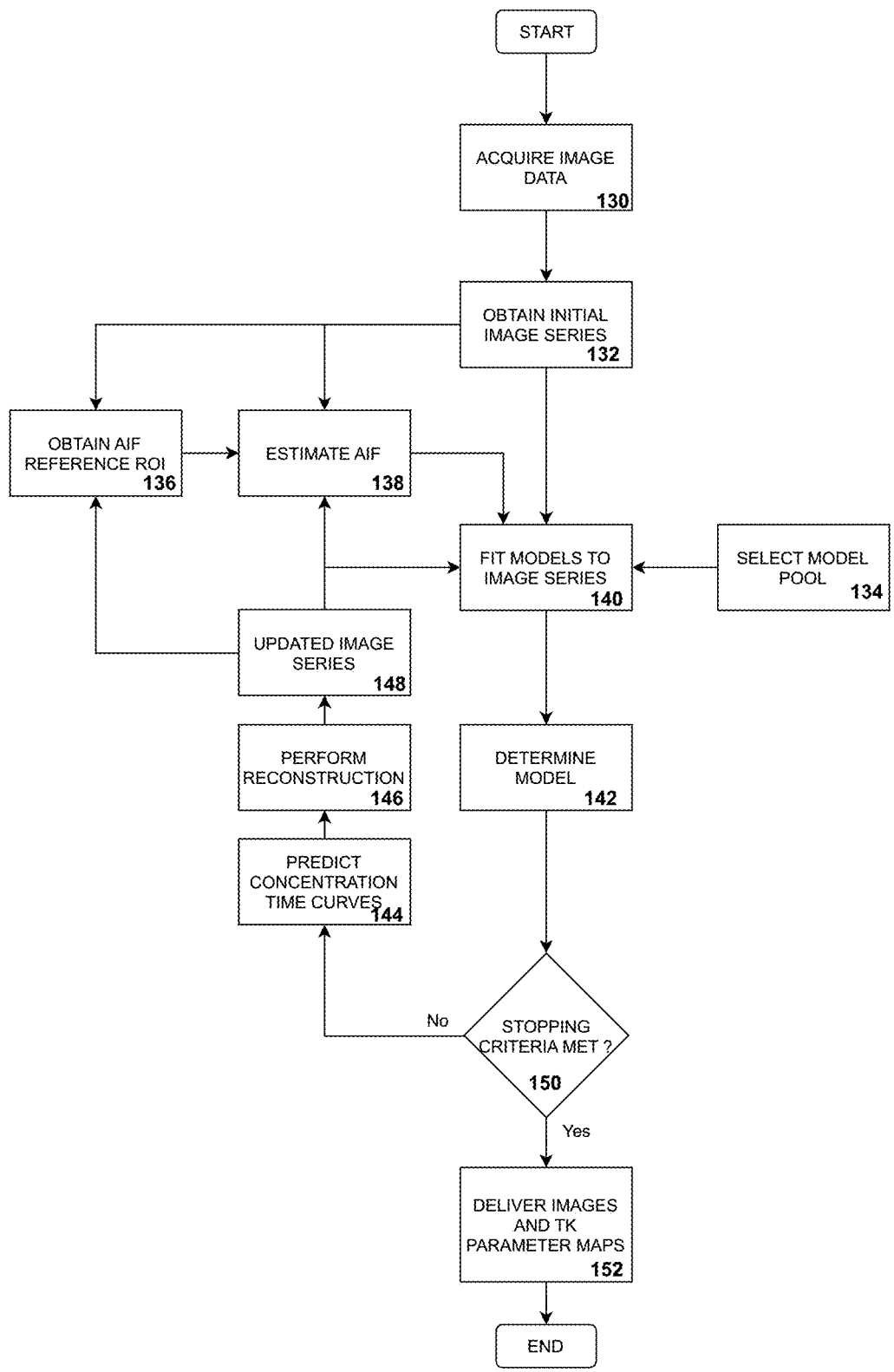
FIG. 1B. Flowchart applying tracer kinetic parameter estimation with automated TK model and reference tissue/vessel selection.

In one variation, the tracer kinetic model can be preselected (e.g., by a user) as depicted in the flow chart of FIG. 1A. In another variation, the tracer kinetic model is automatically identified and selected as depicted in the flowchart of FIG. 1B. For example, the tracer kinetic model is automatically selected by specifying a collection of possible models (nested or not nested) from which a model identification method is applied to select a model for each voxel or region. Examples of such model identification methods include, but are not limited to, model order estimation methods (e.g., information criteria), goodness of fit criteria (e.g., Balvay's criterion/Chi-square criterion, F-statistics, etc.) and the like. In a refinement, the step of selecting a tracer kinetic model includes jointly estimating contrast concentration versus time images and TK parameter maps from under-sampled (k,t) space data for all models in the model pool. Resulting estimates from each model in the model pool are ranked from best to poorest fit based on a goodness-of-fit criterion or information criterion for each voxel or region. For each voxel or region, the model with the highest rank is selected.

With reference to FIG. 1A, measurement data is acquired on MR system following a MR contrast agent injection into patient as shown in Box 100. In Box 102, the initial guess for the dynamic image series is obtained by zero-filling unacquired samples of data in measurement space and applying the data consistency constraint without model consistent, i.e., β=0 (CG-SENSE). Alternatively, all measurement data can be accumulated into one time frame and this reconstructed time frame is copied to all time frames. As depicted in Box 104, the user defines a trace-kinetic model for the estimation of tracer-kinetic parameter maps (e.g., ETK or Patlak). The Region-Of-Interest for AIF/VIF extraction (typically a vessel location) is specified on the initial guess of dynamic image series (Box 106). In Box 108, the AIF/VIF is extracted from the defined ROI for extraction. The tracer-kinetic model is deployed to estimate tracer-kinetic parameter maps from the current estimates of image time series (Box 110). The estimate of the tracer-kinetic parameter maps is passed through the tracer-kinetic model to estimate a current guess of concentration time curves (Box 112). In Box 114, the consistency constraint, i.e., the weighted sum of data consistency and model consistency, is applied to estimate a new estimate of concentration-time curves. As depicted in Box 116, the image time series is updated based on the current estimate of concentration time curves. As suggested by Box 118, steps of Boxes 108-116 5-9 are repeated until the change reconstructed image time series and estimated tracer kinetic parameter maps falls below a predefined threshold or a maximum number of iterations has been reached. Finally, Box 120 indicates that dynamic image time series, AIF/VIF, and tracer-kinetic parameter maps are delivered.

With reference to FIG. 1B, measurement data is acquired on MR system following a MR contrast agent injection into patient as depicted in Box 130. As depicted in Box 132, the initial guess for the dynamic image series is obtained by zero-filling unacquired samples of data in measurement space and applying the data consistency constraint without model consistent, i.e., β=0 (CG-SENSE). Alternatively, all measurement data can be accumulated into one time frame and this reconstructed time frame is copied to all time frames. The user defines a trace-kinetic model for the estimation of tracer-kinetic parameter maps (e.g., ETK or Patlak) as shown in Box 134. As shown in Box 136, the Region-Of-Interest for AIF/VIF extraction (typically a vessel location) is estimated based on the current estimate of the image time series. This is done by ranking potential candidate voxels based on user-specified criteria and selected best candidates. In Box 138, the AIF/VIF is extracted from the defined ROI for extraction. As depicted in Box 140, all candidate models in the collection of tracer-kinetic models are deployed to estimate a collection of tracer-kinetic parameter maps from the current estimates of image time series. Box 142 shows that based on user-defined goodness-of-fit criteria all tracer-kinetic maps in the collection are assessed and the associated models are ranked according to appropriateness to predict the current estimate of image time series. The highest-ranking model is selected for each voxel or region. As depicted in Box 144, the estimate of the tracer-kinetic parameter maps is passed through the highest-ranking tracer-kinetic model in each voxel or region to estimate a current guess of concentration time curves. As shown in Box 146, the consistency constraint, i.e., the weighted sum of data consistency and model consistency, is applied to estimate a new estimate of concentration-time curves. The image time series is then updated based on the current estimate of concentration time curves as shown in Box 148. Box 150 suggests that steps 136-148 are repeated until the change reconstructed image time series and estimated tracer kinetic parameter maps falls below a predefined threshold or a maximum number of iterations has been reached. Finally, image time series, AIF/VIF, and tracer-kinetic parameter maps are delivered as shown in Box 152.

In one variation, a manually selected reference tissue mask for extraction of patient specific AIF/VIF from MRI data is used. In another variation, reference tissue and vessels for data extraction is automatically determined (e.g., in each iteration) based on the current image series. This can be done with a variety of criteria: choosing voxels of peak enhancement (e.g., relative or absolute peak enhancement), comparison to reference (population based) AIF, model order estimation methods like information criteria, goodness of fit criteria like Balvay's criterion/Chi-square criterion, and the like. The candidate voxels are ranked based on the selected criteria from best to worst. The AIF/VIF is extracted from the voxels with highest ranking.

As set forth above, the present embodiment applies a tracer kinetic model. Examples of suitable tracer models are the Patlak and extended Tofts-Kety (ETK) model as set forth in P. S. Tofts, G. Brix, D. L. Buckley, J. L. Evelhoch, E. Henderson, M. V Knopp, H. B. Larsson, T. Y. Lee, N. a Mayr, G. J. Parker, R. E. Port, J. Taylor, and R. M. Weisskoff, "Estimating kinetic parameters from dynamic contrast-enhanced T(1)-weighted MRI of a diffusable tracer: standardized quantities and symbols. "J. Magn. Reson. Imaging, vol. 10, no. 3, pp. 223-32, Sep. 1999; and Parker, G. J. and Buckley, D. L., 2005. Tracer kinetic modelling for T1-weighted DCE-MRI. In *Dynamic contrast-enhanced magnetic resonance imaging in oncology* (pp. 81-92). Springer Berlin Heidelberg; the entire disclosures of these publications is hereby incorporated by reference. In general, the Patlak and ETK having kinetic parameters: $K^{trans}$ which is a transfer constant from blood plasma into extracellular extravascular space (EES) and $v_p$ which is fractional plasma volume. The ETK model also has kinetic parameters $K^{ep}$ which is a transfer constant from EES back to the blood plasma and $v_e$ which is a fractional EES volume ($v_e = K^{trans}/K^{ep}$). The concentration for the contrast agent in this model is calculated from:

$$\frac{dC_t}{dt} = K^{trans}(C_p - C_e) = K^{trans}(C_p - C_t/v_e)$$

where
$C_t$ is the equilibrium concentration of contrast agent in whole tissue;
$C_p$ is the equilibrium concentration of contrast agent in plasma;
$C_e$ is the equilibrium concentration of contrast agent in extracellular extravascular space.

In the simple Toft model, the contrast concentration in the whole tissue can be determined from:

$$C_t(t) = K^{trans} \int_0^t C_p(\tau) e^{-(K^{trans}/v_e)(t-\tau)} d\tau$$

When $v_p$ is considered such as in the ETK model, the contrast concentration in whole tissue can be determined from:

$$C_t(t) = v_p C_p(t) + K^{trans} \int_0^t C_p(\tau) e^{-(K^{trans}/v_e)(t-\tau)} d\tau$$

When the time dependent concentrations, ie, $C_t$ and $C_p$, are known, these equations can be inverted to estimate the kinetic parameters. Additional details for converting TK parameter (e.g., $K^{trans}$, $v_p$) maps to contrast concentration over time using the Patlak model is provided by P. S. Tofts, G. Brix, D. L. Buckley, J. L. Evelhoch, E. Henderson, M. V Knopp, H. B. Larsson, T. Y. Lee, N. a Mayr, G. J. Parker, R. E. Port, J. Taylor, and R. M. Weisskoff, "Estimating kinetic parameters from dynamic contrast-enhanced T(1)-weighted MRI of a diffusable tracer: standardized quantities and symbols. "J. Magn. Reson. Imaging, vol. 10, no. 3, pp. 223-32, Sep. 1999 and Patlak C. S., Blasberg R. G., Fenstermacher J. D. Graphical evaluation of blood-to-brain transfer constants from multiple-time uptake data. J. Cereb. Blood Flow Metab. 1983; 3:1-7; the entire disclosures of these publications is hereby incorporated by reference.

As set forth above, the dynamic images and the tracer kinetic parameter maps are estimated jointly by enforcing a consistency constraint. The consistency constraint includes a weighted sum of a data consistency component and a model consistency component. The data consistency component assesses how well the acquired imaging data (e.g., raw or Fourier transformed magnetic resonance data) for each voxel in a Field Of View is approximated by the dynamic images calculated from the estimate of concentration-time curves of the contrast agent for each voxel in a Field Of View. Therefore, a first difference can be between the acquired imaging data for each voxel in a Field Of View and data calculated from the estimated concentration-time curves for each voxel in a Field Of View. Similarly, the model consistency component assesses how well the concentration-time curves calculated from the estimate of the tracer kinetic model and its plurality of parameters approximate measured concentration-time curves of the contrast agent for each voxel in a Field Of View. Therefore, a second difference can be determined between the measured concentration-time curves for each voxel in a Field Of View and concentration-time curves calculated from the tracer kinetic model for each voxel in a Field Of View. The consistency constraint seeks to minimize the combination of both differences (e.g., see the β parameter below).

In a variation, the consistency constraint is provided by the minimization (i.e., a a least squares optimization) represented by Equation 1:

$$(C, \theta) = \underset{C, \theta}{\mathrm{argmin}} \|UFE(\psi C + S_0) - y\|_2^2 + \beta \|P(\theta) - C\|_2^2 \qquad [1]$$

where:
ψ is a signal operator which converts concentration-time-curves (per voxel) C of a contrast agent to an image intensity time series;
U is an under-sampling mask;
F is a Fourier transform, and in particular, the discrete Fourier transform matrix or a Fast-Fourier-Transform (FFT) algorithm;
E is a sensitivity encoding matrix providing the spatial relative sensitivities of the pickup coils;
$S_0$ is image intensity for each voxel prior to contrast agent arrival;
y is under-sampled magnetic resonance imaging data:
C is a measured concentration-time curves of the contrast agent for each voxel in the Field Of View;
P(θ) is a predicted concentration distribution of the contrast agent from the selected tracer kinetic model;
β is a penalty or weight factor for the model consistency component; and
θ are tracer kinetic parameters such $K^{trans}$ and $v_p$ for the Patlak and ETK models and $K^{ep}$ and $v_e$ for the ETK as described below.

It should be noted that U, F, and E are linear operators which can be expressed as matrices, while ψ can be either a linear or non-linear operator. $S_0$ is expressed as matrix with each matrix entry being a value for a spatial point or voxel. C is expressed as matrix with each matrix entry being a value for a spatial point or voxel and time point. In equation 1, the first $l_2$ norm represents the data consistency component and the second $l_2$ norm represents model consistency component.

In another variation, the arterial input function is smoothed or forced to fit a model. In this regard, smoothing, regularization, and regression include any form of variation penalty, e.g., constraints applied to temporal derivatives and frequency spectra of the input function and its epochs, spatial smoothing filters, e.g., (weighted) averaging over or preferential selection from multiple ROI voxels, and regression to a pre-specified, parameterized functional form for the input function, e.g., sum of exponentials, sum of gamma-variates, sum of sigmoids, or a mixture thereof.

In most applications, all steps of the method set forth above are repeated for multiple slices through said object being imaged and three-dimensional image data are reconstructed.

It should also be appreciated that the methods set forth herein can be applied to any dynamic contrast imaging technique such dynamic contrast magnetic resonance imaging and dynamic contrast positron emission tomography.

Figure 2:
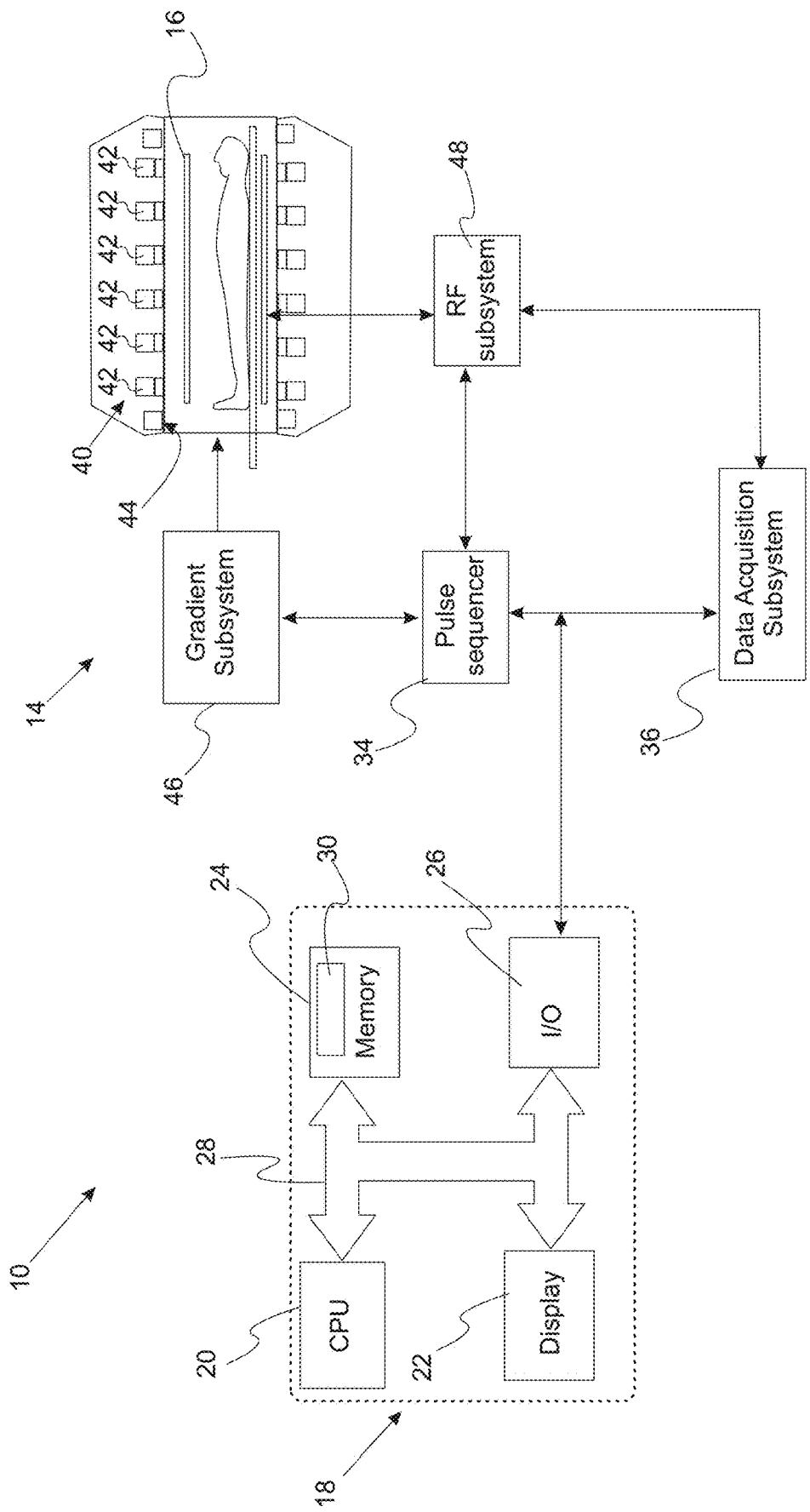
FIG. 2. Schematic illustration of MRI system for DCE-MRI examination using the methods set forth herein and in particular, the methods of FIG. 1A.

In another embodiment, a magnetic resonance system, and in particular, an MRI system for improving dynamic contrast enhanced imaging is provided. The system advantageously implements the methods set forth herein. With reference to FIG. 2, imaging system 10 includes magnetic resonance imaging system 14 which can be any MR imaging system generating data with T1 or T2-weighted contrast. Typically, system 14 implements a standard SPGR imaging sequence (T1-weighted contrast) with a modifiable sampling trajectory. Magnetic resonance imaging system 14 includes coils 16 from which the (k, t) space data is collected. Imaging system 10 also includes a programmable computer 18 to implement the method set forth above. Computer 18 includes central processing unit (CPU) 20, memory 22, display 24 and input/output interface 26 which communicates over buses 28. Computer 18 communicates with magnetic resonance imaging system 14 and input devices 30 such as a keyboard and mouse via input/output interface 26. In one variation, memory 22 includes one or more of the following: random access memory (RAM), read only memory (ROM), CDROM, DVD, disk drive, tape drive. The method of the present variation is implemented by routine 32 that is stored (i.e., encoded) in non-transitory memory 30 and executed by the CPU 20. In a variation, computer 18 is electrically coupled to pulse sequencer 34 and data acquisition subsystem 36 of magnetic resonance system 14. Pulse sequencer 34 is also in electrical communication with data acquisition subsystem 36. Magnetic assembly 40 includes polarizing magnetic coil 42 and gradient coil assembly 44. Pulse sequencer 34 receives instruction from computer 18 to operate a gradient system 46 and a radiofrequency (RF) system 48. RF system 48 includes RF transmitters for this purpose in order to generate the prescribed pulses and one or more receiver channels for receiving signal from coils 16. Gradient waveforms necessary to perform the magnetic pulses set forth above are produced and applied to the gradient system 38, which excites gradient coils in coil assembly 50 to produce the magnetic field gradients and used for position encoding magnetic resonance signals. RF waveforms are applied by the RF system 48 to the RF coil 16, or a separate local coil (not shown), in order to perform the prescribed magnetic resonance pulse sequence. Responsive magnetic resonance signals detected by the RF coil 16 or a separate local coil (not shown), are received by the RF system 48 where they are processed accordingly.

Computer 18, and in particular, CPU 20 in conjunction with magnetic resonance imaging system 14 implements the methods set forth above as follows. Computer 18 send control signals to pulse sequencer 34 to control gradient system 46 to apply a gradient magnetic field pulse from polarizing magnetic coil 42 to a subject 56 along a first direct. A subject who has been administered a contract agent is placed in this gradient magnetic field. Computer 18 also sends control signals to pulse sequencer 34 to RF system 46 to apply an excitation radiofrequency pulse to the subject during the first gradient magnetic field pulse where the excitation radiofrequency pulse is resonant with a region in the subject. Computer 18 also sends control signals to pulse sequencer 34 to control gradient system 46 to apply gradient magnetic field pulses to the subject after the first gradient magnetic field pulse in order to provide spatial encoding. RF system 46 receives an output signal from the subject 56 during the second gradient magnetic field pulse such that magnetic resonance imaging data is collected from the subject for a tissue or organ. This output signal is ultimately transferred to computer 18 for processing. Computer 18, and in particular CPU, applies a selected tracer kinetic model to the magnetic resonance imaging data to estimate tracer kinetic parameter maps; and applying the tracer kinetic model to the magnetic resonance imaging data to estimate tracer kinetic parameter maps; and reconstructing tracer kinetic maps and dynamic images from the tracer kinetic parameter maps, wherein a consistency constraint is applied to reconstruct the tracer kinetic maps and dynamic images, the consistency constraint including a sum of a data consistency component and a model consistency component. The tracer kinetic model can be user selected in advance or automatically selected or determined by computer 18. Additional details regarding all of the steps implemented the system and in particular computer 18 are set forth above.

In a variation, magnetic resonance imaging system 14 generates magnetic resonance imaging data from a subject for a tissue or organ. As set forth above, a magnetic resonance contrast agent is administered prior to the generation and collection of the imaging data. Programmable computer 18 is operable to execute steps of collecting the magnetic resonance imaging data from the subject and reconstructing dynamic images and tracer kinetic maps from the magnetic resonance imaging data as set forth above. Computer 18 is further operable to apply a consistency constraint as set forth above. Finally, the steps of reconstructing dynamic images, applying the tracer kinetic model, and applying the consistency constraint are alternately performed until converging on a set of dynamic images and tracer kinetic parameter maps. Computer 18 can be further operable to select a tracer kinetic model to be applied to the magnetic resonance imaging data where the tracer kinetic model being defined by a plurality of tracer kinetic parameters. Advantageously, the programmable computer is also operable to determine an arterial input function or vascular input function from the magnetic resonance imaging data, wherein the arterial input function includes a time variation of a magnetic resonance contrast agent at one or more predetermined locations in an artery of the subject. Characteristically, the arterial input function is taken as surrogate for the vascular input function with the arterial input function being determined as a function of time. In some variations, reference tissue and vessels for AIF extraction are automatically selected in each iteration based on a current image series. In this regard, reference tissue and vessels for AIF extraction can be automatically selected from voxels of peak enhancement or by comparison to reference (population based) AIF or by a model order estimation method. In another refinement, the programmable computer is operable to identify and select a tracer kinetic model from a library of tracer kinetic models. In still other refinement, computer 18 is operable to automatically selected a tracer kinetic model by specifying a collection of possible models (nested or not nested) from which a model identification method is applied to select a model for each voxel or region. In some variation, computer 18 is operable to simultaneously reconstruct tracer kinetic parameter maps and the dynamic images. As set forth above, the tracer kinetic model can be a Patlak model or an extended Tofts model.

Additional details of the present invention can be found in Y Guo, S G Lingala, Y Bliesener, R M Lebel, Y Zhu, K S Nayak. Joint arterial input function and tracker kinetic parameter estimation from under-sampled DCE-MRI using a model consistency constraint. Magnetic Resonance in Medicine. 79(5):2804-2815. May 2018; the entire disclosure of which is hereby incorporated by reference.

The following examples illustrate the various embodiments of the present invention. Those skilled in the art will recognize many variations that are within the spirit of the present invention and scope of the claims.

THEORY

Model Consistency Constraint

This method jointly estimates contrast concentration versus time images (C) and TK parameter maps ($\theta$) from the under-sampled data (y) by solving the following least-squares problem:

$$(C, \theta) = \underset{C,\theta}{\mathrm{argmin}} \|UFE(\psi C + S_0) - y\|_2^2 + \beta \|P(\theta) - C\|_2^2 \qquad [2]$$

The first $l_2$ norm represents data consistency, where C should be consistent with the measured data y by $\Psi$ (signal equation), U (under-sampling mask), F (Fourier transform), and E (sensitivity encoding). $S_0$ is the first temporal frame images that are fully sampled. The second $l_2$ norm represents model consistency, where C is consistent to the forward modeling (P) of TK parameter maps (Patlak, eTofts etc.). This formulation can be simplified to:

$$(C, \theta) = \underset{C,\theta}{\mathrm{argmin}} \|AC - b\|_2^2 + \beta \|P(\theta) - C\|_2^2 \qquad [3]$$

where A=UFE$\Psi$ represents data consistency modeling, b=(y-UFES$_0$) is the known data. To solve the least-square optimization problem in Equation [2], we alternatively solve for each variable while keeping others constant. For each iteration n, $$C^{n+1} = \underset{C}{\mathrm{argmin}} \|AC - b\|_2^2 + \beta \|P(\theta^n) - C\|_2^2 \qquad [4]$$

$$\theta^{n+1} = P^{-1}(C^{n+1}) \qquad [5]$$

Note that Equation [3] is regularized SENSE reconstruction with an $l_2$ norm constraint that can be solved efficiently using conjugate gradients (30). Equation [4] is backward TK modeling that can be solved using any DCE-MRI modeling toolbox. Because forward modeling (P) and backward modeling (P$^{-1}$) are used iteratively, the modeling solver should not utilize linearization or other forms of approximation. For example, ROCKETSHIP (31) and TOPPCAT (32) are two suitable solvers. Detailed sub steps and variants of Equations [3] and [4] are provided in the Appendix.

Joint AIF and TK Parameter Estimation

The proposed formulation allows for joint estimation of the patient-specific AIF. Equation [2] can be modified to estimate C, θ, and AIF from under-sampled data by solving the following least-squares problem:

$$(C, \theta, AIF) = \underset{C,\theta,AIF}{\operatorname{argmin}} \|AC - b\|_2^2 + \beta \|P(\theta, AIF) - C\|_2^2 \quad [6]$$

Similar to the above, we solve each variable alternatively as follows ($n^{th}$ iteration):

$$C^{n+1} = \underset{C}{\operatorname{argmin}} \|AC - b\|_2^2 + \beta \|P(\theta^n, AIF^n) - C\|_2^2 \quad [7]$$

$$\theta^{n+1}, AIF^n = P^{-1}(C^{n+1}) \quad [8]$$

Equation [7] is backward TK modeling from contrast concentration including pat-AIF estimation. This can be performed by identifying an arterial ROI once, using the time-averaged image or postcontrast image. Within each iteration, it is then possible to: 1) apply this ROI to C to estimate the AIF (averaging the pixels) and 2) use the updated AIF during TK modeling. This is a common procedure in TK modeling for DCE-MRI. The only difference is identification of the arterial ROI before the reconstruction of the dynamic images.

Theoretical Benefits

The proposed method formulates model consistency as a constraint with a penalty β and decouples it from data consistency. There are multiple benefits of this formulation: 1) algorithm complexity is reduced compared to recently proposed direct reconstruction techniques that require complex cost function gradient evaluations (14,20,33); 2) different TK models can easily be included in this formulation, as described above; 3) patient-specific AIFs can be estimated jointly with TK maps, as described above; and 4) the penalty β can allow for TK model deviation, reducing errors that may be caused by strict model enforcement (29). This study specifically demonstrates items #2 and #3.

METHODS

Data Sources

Digital Reference Object

Anatomically realistic brain tumor DCE-MRI DRO was generated based on the method and data provided by Bosca and Jackson (34). The extended Tofts (eTofts) model was used to generate contrast concentration curves with known TK parameter maps and pop-AIF (27). Coil sensitivity maps measured on our MRI scanner (3T, eight-channel head coil) were coregistered to the DRO and used to generate realistic MRI k-space data (35). Gaussian noise was added to the image space to simulate noise levels typical of DCE-MRI at 3T and 1.5T.

Retrospective

Nine anonymized fully sampled brain tumor DCE-MRI raw data sets were obtained from patients who had undergone routine brain MRI examinations with contrast (including DCE-MRI) at our institution. The study protocol was approved by our Institutional Review Board. The acquisition was based on a 3D Cartesian fast spoiled gradient echo (SPGR) sequence using the following parameters: field of view=22×22×4.2 cm$^3$, spatial resolution=0.9×1.3×7.0 mm$^3$, temporal resolution=5 s, 50 time frames, eight receiver coils, flip angle=15°, echo time =1.3 ms, repetition time=6 ms. DESPOT1 was performed before DCE-MRI, with a flip angle of 2°, 5°, and 10° to estimate precontrast T$_1$ and M0 maps. The contrast agent, gadobenate dimeglumine [Multi-Hance Bracco Inc.; relaxivity r$_1$=4.39 s$^{-1}$·mM$^{-1}$ at 37° C. at 3T (36)] was administered with a dose of 0.05 mmol/kg, followed by a 20-mL saline flush in the left arm via intravenous injection.

Prospective

Prospectively under-sampled data were acquired in one brain tumor patient (male, age 65 years, glioblastoma) with Cartesian golden-angle radial k-space sampling (9,37). 3D SPGR data were acquired continuously for 5 min. Whole-brain coverage was achieved with a field of view of 22*22*20 cm$^3$ and spatial resolution of 0.9*0.9*1.9 mm$^3$. The prospective study protocol was approved by our Institutional Review Board. Written informed consent was provided by the participant.

Demonstration of TK Solver Flexibility

To demonstrate TK solver flexibility, DRO data was retrospectively under-sampled using a randomized golden-angle sampling pattern at R=60× (37). Gaussian noise was added to the image space, creating signal-to-noise ratio (SNR) levels of 20 and 10 (white matter based) for simulation of DCE-MRI image quality at 3T and 1.5T. The proposed method with eTofts modeling was used to reconstruct TK parameter maps at R=60 × and SNR=20 and 10, respectively. An in-house gradient-based algorithm and an open-source TK modeling toolbox, ROCK-ETSHIP (31), were used for the eTofts solver in the proposed algorithm (Eq. [4]). Tumor ROI K$^{trans}$ correlation coefficient, R$^2$ and normalized root mean-squared-error (nRMSE, normalized by the 90th percentile value within the tumor ROI) between the estimated and true values were calculated and compared. Note that tumor ROI 90th percentile K$^{trans}$ value has been found to be a sensitive and clinically valuable DCE-MRI biomarker (38,39), hence normalization of RMSE by this value. TK maps estimated from the noisy fully sampled images (SNR=20, R=1×) were also compared with the true TK maps to evaluate the performance of the proposed method with respect to errors found in conventional DCE-MRI.

Demonstration of TK Model Flexibility

The nine fully sampled patient data were fitted to the Patlak and eTofts models to calculate the model fitting error, and an F-test was performed in the tumor ROI to determine whether the Patlak or eTofts model is the most appropriate fit (23-25). In the F-test (40,41), the null hypothesis is that the two samples of sum-of-squared modeling errors were drawn from the same pool. The failure of this hypothesis leads to acceptance of the higher-order model. Thus, for each pixel, the F-test will reveal whether a higher-order model (eTofts model) should be used (23-25). If more than 50% of the tumor pixels were appropriately fitted for a certain model, this model was selected for the data set. We reconstructed the corresponding TK parameter maps for fully sampled data (used as reference) and at under-sampling rates of 20×, 60×, and 100 × for all nine cases. A randomized golden-angle sampling pattern (37) was used in the $k_x$-$k_y$ plane, simulating $k_y$-$k_z$ phase encoding in a 3D whole-brain acquisition. Images were reconstructed using a pop-AIF (27) with patient-specific delay corrected by the delay estimated from k-space center (42). ROI-based $K^{trans}$ nRMSE and $K^{trans}$ histograms were calculated based on the reference $K^{trans}$ maps. $K^{trans}$ histogram skewness and 90th percentile $K^{trans}$ values were also measured for evaluation, as they have been shown to be valuable in the clinical assessment of brain tumors by DCE-MRI (38,39,43).

Demonstration of Joint AIF and TK Estimation

The cases following the Patlak model were reviewed with special attention to vessel signal. Cases that showed significant precontrast inflow enhancement were identified and subsequently excluded. With the remaining cases, we performed joint estimation of AIF and Patlak parameter maps from under-sampled data across sampling rates of 20×, 60×, and 100×. For each under-sampling rate, 15 realizations were generated by varying the initial angle of the golden-angle radial sampling pattern (37). The golden-angle radial sampling with different initial angle will create mostly nonoverlapped k-space coverage, effectively providing different noise realizations with the same noise level (white matter SNR=20). Reconstructed patient-specific AIFs were compared with the fully sampled reference using nRMSE (normalized to the 90th percentile AIF value over time) and bolus peak difference. ROI-based $K^{trans}$ nRMSE (normalized to the 90th percentile $K^{trans}$ value over the tumor ROI) were also calculated for evaluation.

Demonstration with Prospectively Under-Sampled Data

We tested the application of the proposed method for joint AIF and TK parameter estimation on prospectively 30× under-sampled high-resolution whole-brain DCE-MRI data. Five-second temporal resolution was achieved by grouping raw (k,t)-space data acquired within consecutive 5-s intervals, effectively 30× under-sampling compared with Nyquist sampling (44). pat-AIF and TK maps were jointly reconstructed using the proposed model consistency constraint approach. pat-AIF ROI was selected based on time-averaged images. Three-plane of $K^{trans}$ and vp maps and pat-AIF are presented for visual assessment.

RESULTS

Figure 3:
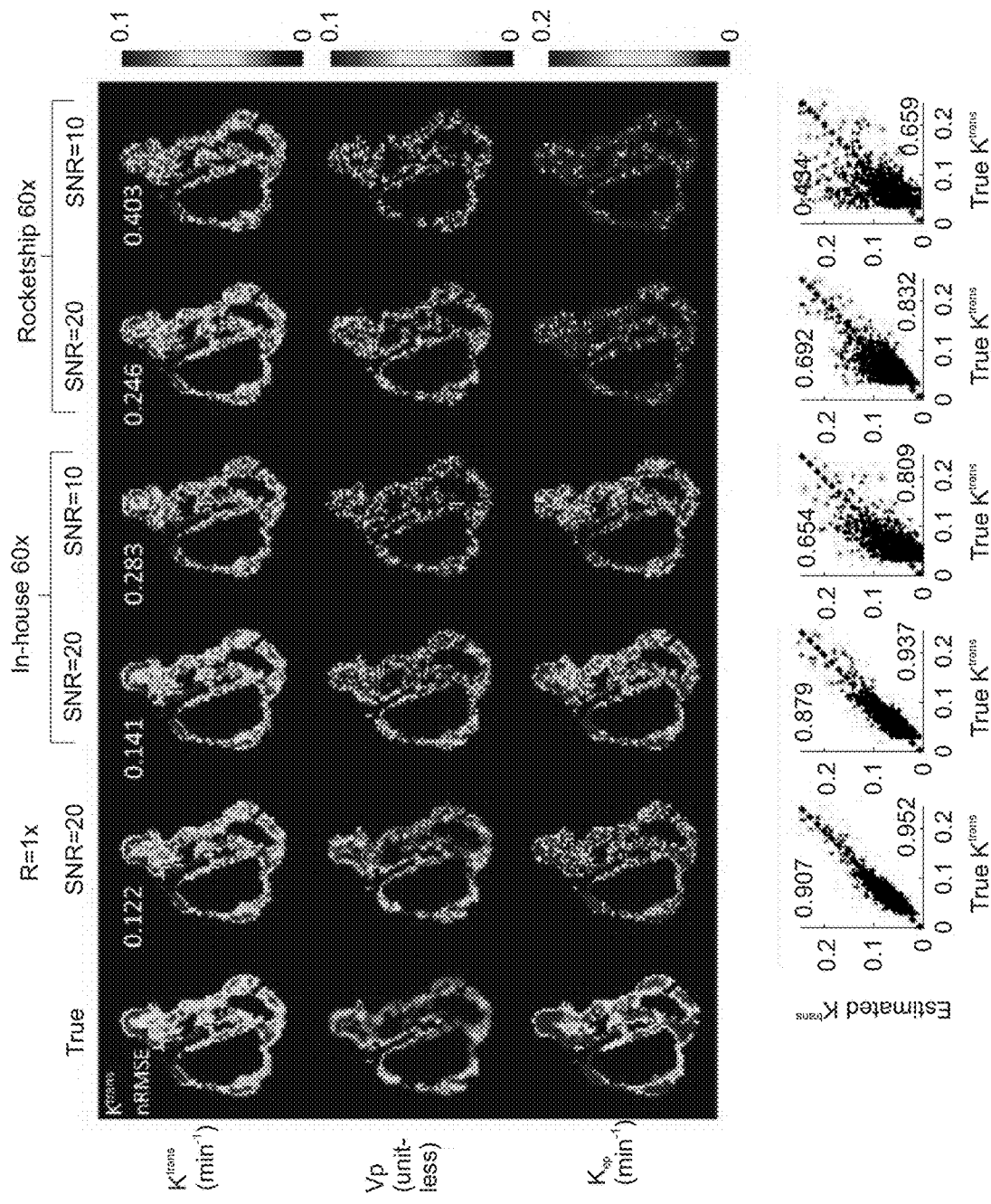
FIG. 3. Results from an anatomically realistic brain-tumor DCE-MRI digital reference object using an in-house solver and the ROCKETSHIP solver, both using the model consistency constraint method. Correlation plots are shown at the bottom of each respective result, where the upper left corner shows the $R^2$ value and the lower right corner shows the correlation coefficient.
Figure 4A:
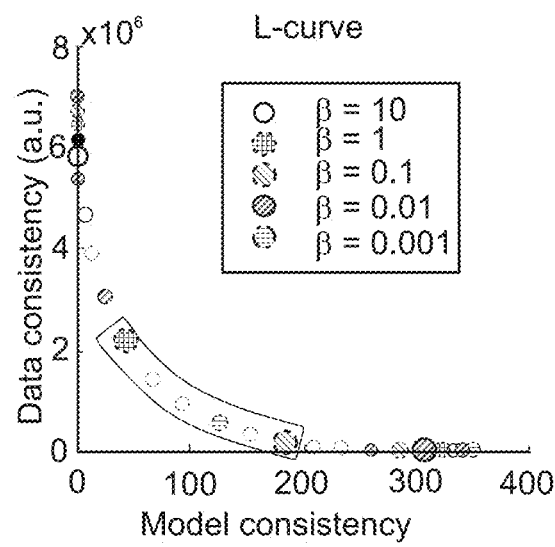
FIGS. 4A, 4B, 4C, and 4D. Performance for different β values at R=20× for one representative in vivo data set FIG. 5. TK maps reconstructed for different β values using the case described in FIG. 4. Tumor ROI nRMSE ($K^{trans}$) are 0.102, 0.073, 0.072, 0.098, and 0.105 for 3 values 10, 1, 0.1, 0.01, and 0.001, respectively.
Figure 4B:
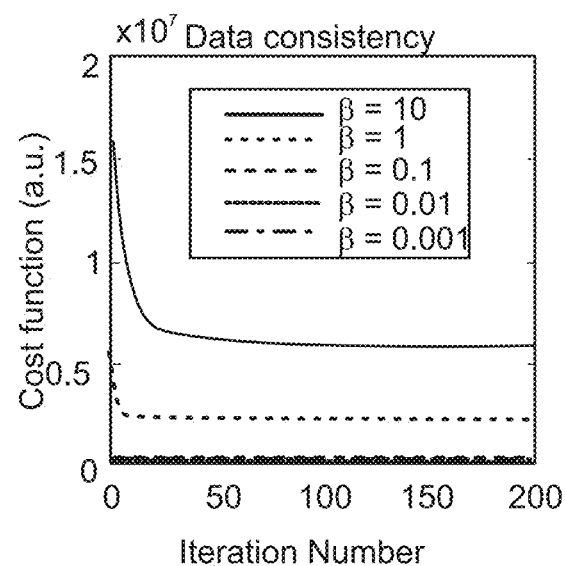
Figure 4C:
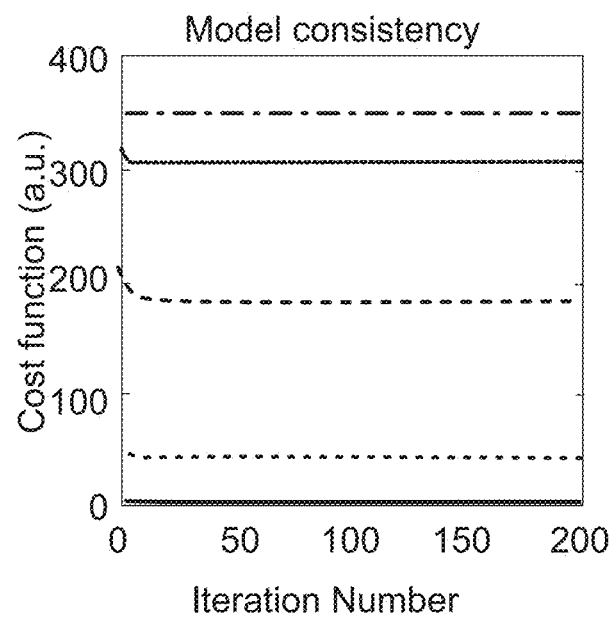
Figure 4D:
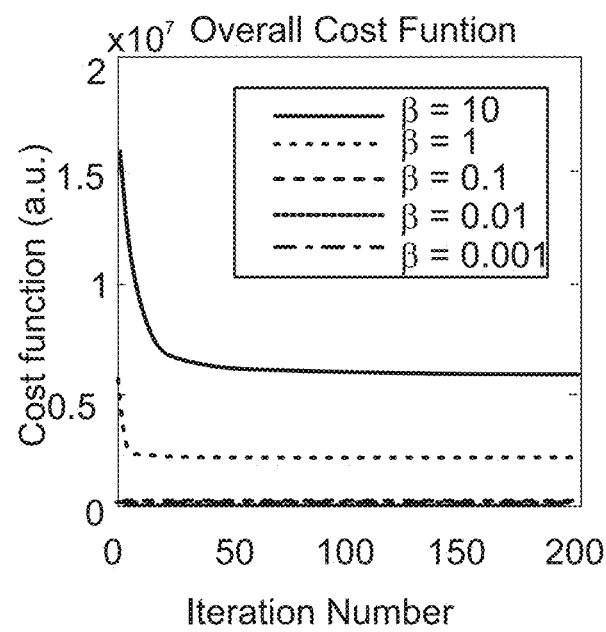
Figure 5:
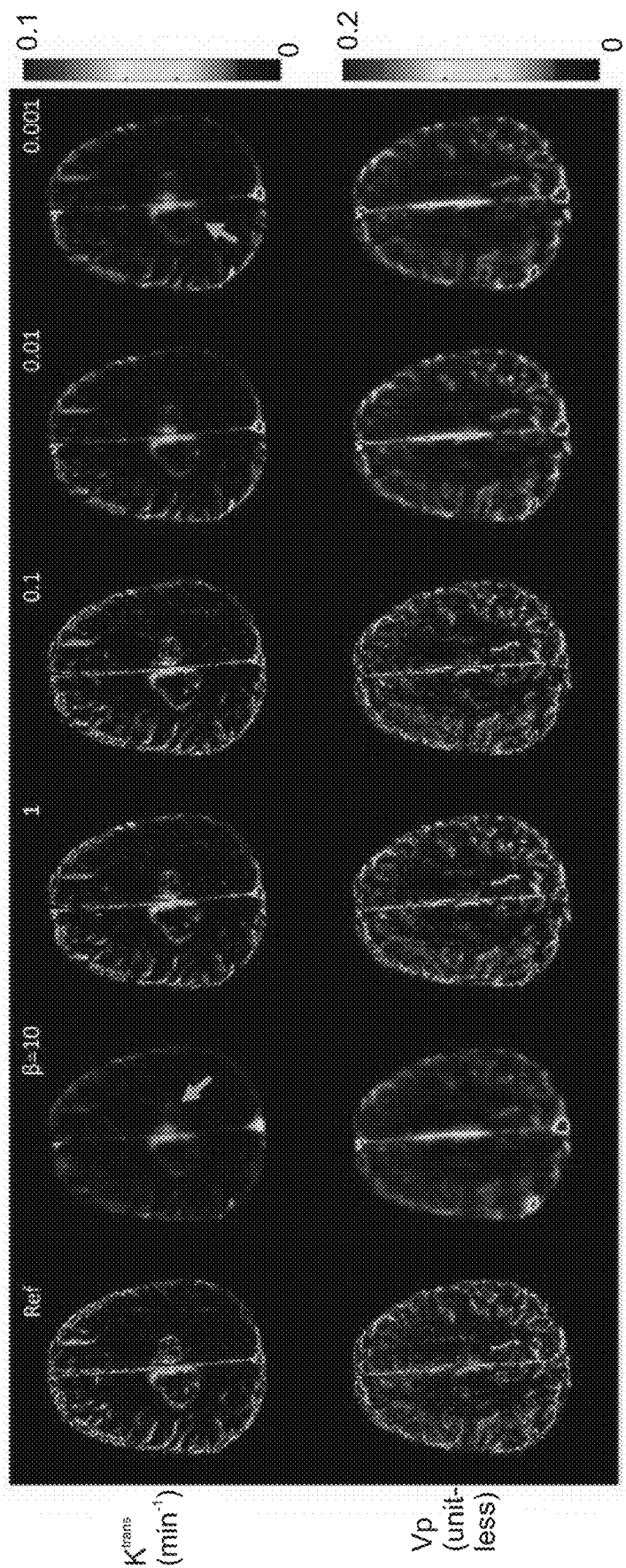

FIG. 3 shows the DRO reconstruction results at R=60× for SNR=20 and 10. R=60× were tested at white matter SNR level of 20 and 10. Tumor ROI $K^{trans}$ nRMSE (normalized to 90th percentile value) were shown on the upper left corner of respective $K^{trans}$ maps. The eTofts model was used to generate the simulated DCE-MRI data, and also for model-based reconstruction. TK maps estimated from fully sampled (R=1×) noisy images are also shown to evaluate the performance in the context of normal DCE-MRI modeling with noise. $\beta$=0.1 and iteration=100 were chosen based on prior experiments. Computation time for the conversion from concentration versus time to TK maps was 3.44 s for the in-house gradient-based method, and 31.62 s for ROCKETSHIP with parallel computing turned on (four workers). Pixel-wise correlation plots between the true and estimated $K^{trans}$ values are shown at the bottom row, with calculated $R^2$ at the upper left corner, and correlation coefficient at the lower right corner. Both methods were able to restore $K^{trans}$ maps with less than 50% error, and the in-house solver was able to restore the TK maps at the quality close to fully sampled noisy results. The ROCKETSHIP solver is more sensitive to increased noise level, especially for $K_{ep}$ and vp maps. These results show that the proposed method can restore TK maps from highly under-sampled data (R=60×) with quality close to modeling results from fully sampled noisy images. It also shows that this method is compatible with a third-party TK solver. Both methods were able to restore $K^{trans}$ maps with less than 50% nRMSE, whereas the ROCKETSHIP solver yielded $K^{trans}$ maps with higher errors, especially at SNR=10. $K_{ep}$ and vp maps are more sensitive to noise, especially when using the ROCKETSHIP solver FIGS. 4 and 5 illustrate the impact of regularization parameter $\beta$ for one representative in vivo brain tumor dataset, using the Patlak model, at R=20×. In FIG. 4(A), the l-curve shows that $\beta$ value controls the balance between model and data consistency. In FIG. 4(B-D), convergence of the cost function to within 1% of its final value required 116, 24, 10, 4, and 2 iterations for $\beta$ values of 10, 1, 0.1, 0.01, and 0.001, respectively. The actual reconstructed TK maps for different $\beta$ values are shown in FIG. 5. The cost function values as a function of iteration number, l-curve, and the final reconstructed TK maps are plotted for different $\beta$ values. A large $\beta$ resulted in slow convergence, whereas a smaller $\beta$ provided fast convergence. This behavior was expected, as ill-conditioning of the problem in Equation [3] increases with $\beta$ (45). TK maps obtained with a large $\beta$ showed poor fidelity as data consistency was violated, whereas the maps with a small $\beta$ were equivalent to a SENSE reconstruction without constraints and demonstrated g-factor-related artifacts at R=20×. The L-curve shows the balance between the data consistency and model consistency, based on which of the $\beta$ values in the range of 0.1 to 1 (green highlighted) show similar performance. We then tuned the $\beta$ value in this range for different cases. We found the acceptable range to be roughly 1 order of magnitude and to be consistent among the four cases that we examined carefully. As shown in FIG. 5, reconstruction with small $\beta$ values converged quickly and is closer to a SENSE reconstruction with associated g-factor losses and under-sampling artifacts. Reconstruction with large $\beta$ values shows slow convergence and provides less accurate TK maps due to the data consistency being violated.

Figure 6:
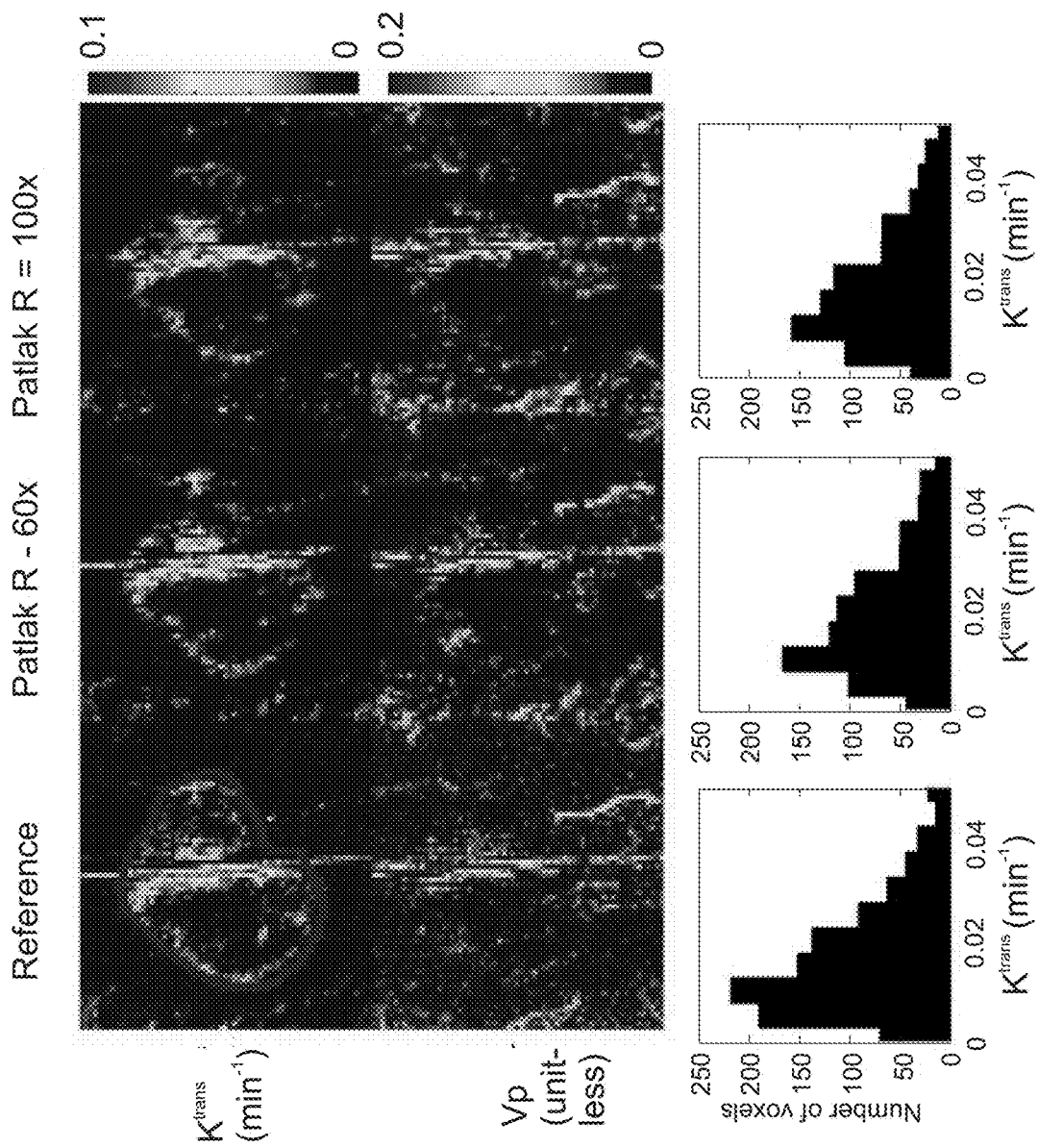
FIG. 6. Reconstruction of the TK maps of one representative in vivo brain tumor case using the Patlak model at R=60× and 100×.
Figure 7:
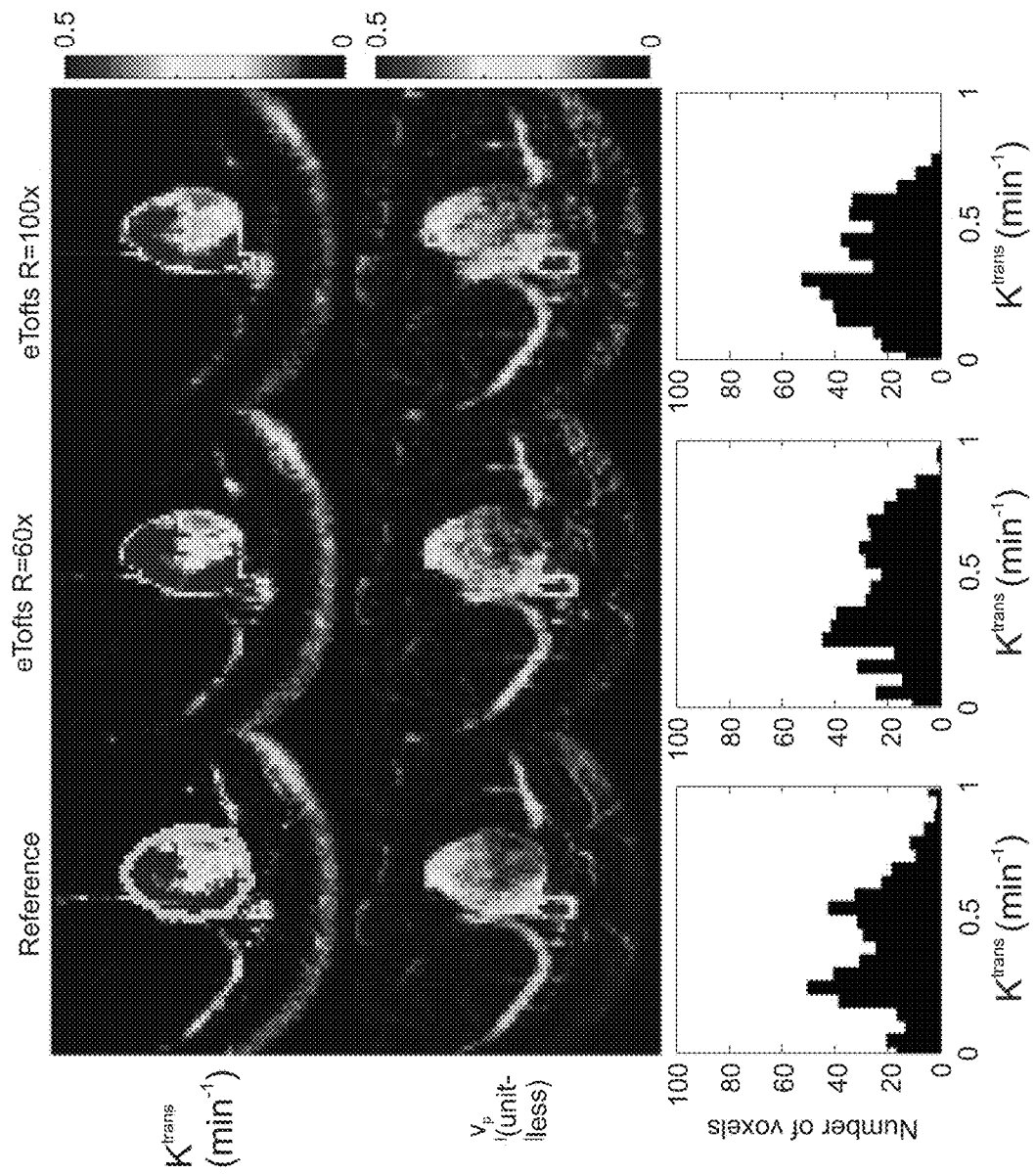
FIG. 7. Reconstruction of the TK maps of one representative in vivo brain tumor case using the eTofts model at R=60× and 100×.

Based on the tumor ROI F-test, the Patlak model was appropriate for six in vivo cases, whereas the e-Tofts model was appropriate for three in vivo cases. FIGS. 6 and 7 show representative cases of Patlak and eTofts model, respectively, at R=60× and R=100×. $K^{trans}$ and vp maps on the zoomed-in tumor region are shown (Kep for eTofts is not shown). Histograms of the $K^{trans}$ values within the tumor ROI are plotted for the respective cases (bottom row). FIG. 8 shows quantitative evaluation of all the in vivo reconstruction results focusing on $K^{trans}$ values. For Patlak model reconstruction, the 90th percentile Ktrans values matched well with the reference values across all cases and, the histogram skewness was also reasonably matched. Across all cases and under-sampling rates, nRMSE was less than 32%. For the eTofts model, the 90th percentile $K^{trans}$ values matched well with reference for one case and had larger deviation for the other cases at R=100×. The nRMSE also increased considerably as the under-sampling rate was increased.

Figure 9:
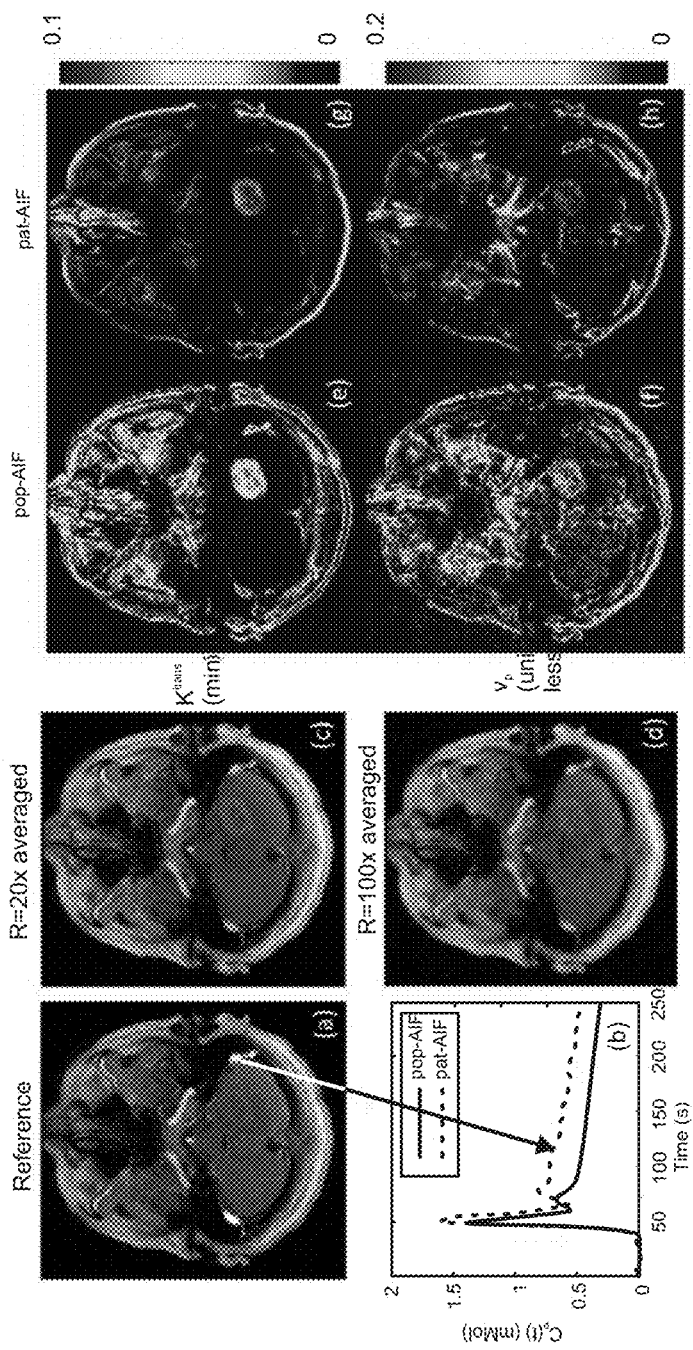
FIG. 9. Extraction of pat-AIF (a-d) resulting in different TK maps (e-f).
Figure 10:
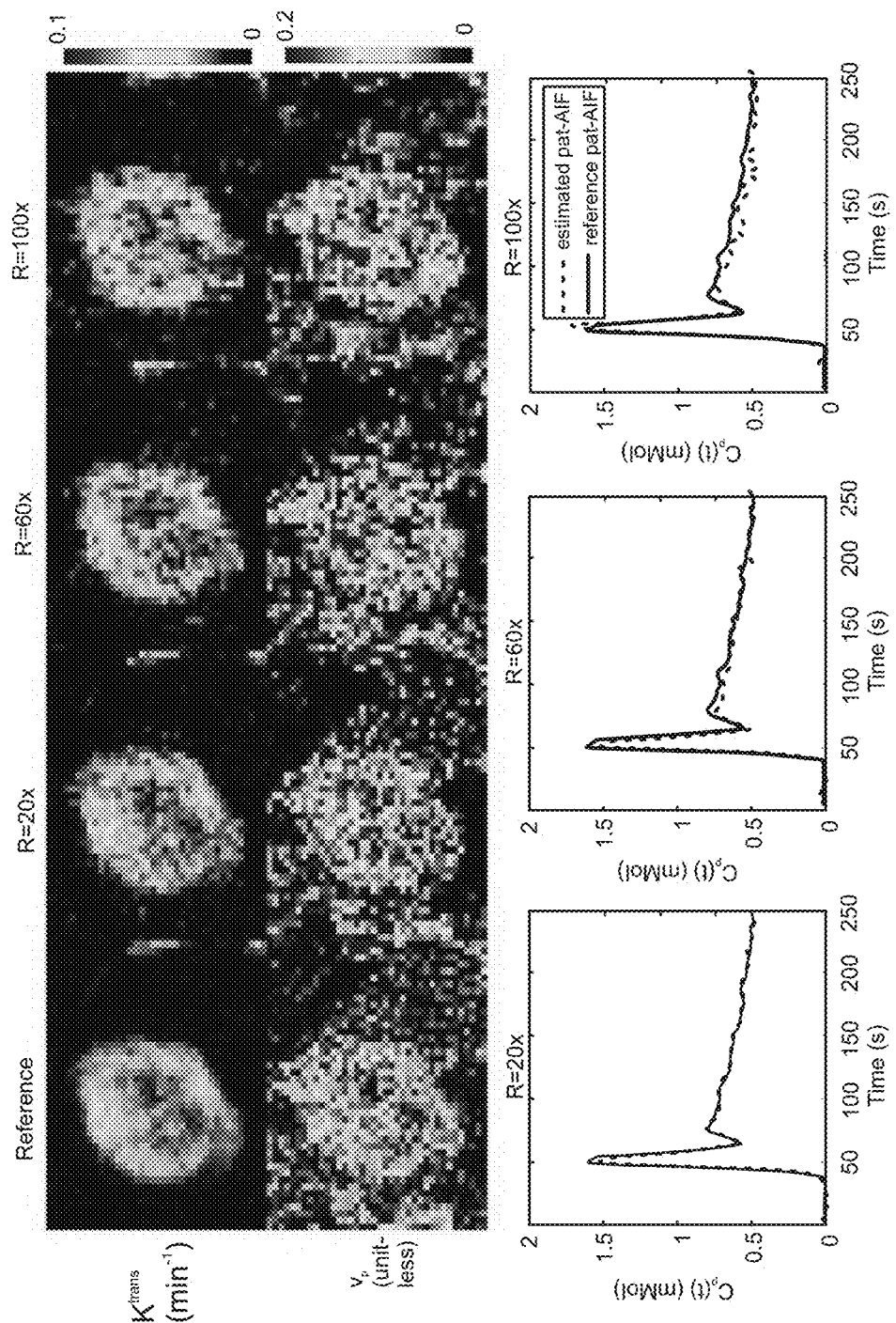
FIG. 10. Joint reconstruction of TK maps and AIF at R=20×, 60×, and 100× for one representative in vivo case.

FIG. 9 shows the selection of AIF ROI from under-sampled data, the comparison of pop-AIF and pat-AIF, and the resulting TK maps in one representative in vivo data set. This figure shows that the ROI of pat-AIF can be easily selected based on average of under-sampled data. This ROI can then be used for joint reconstruction of AIF and TK parameters in the proposed method. FIG. 10 shows the reconstruction results of TK maps and pat-AIF (same case as FIG. 9) at different under-sampling rates. Compared with the AIF extracted from fully sampled data, the proposed method was able to provide clear depiction of AIF peak up to R=100×, with good-quality TK maps restored at the same time.

Figure 11A:
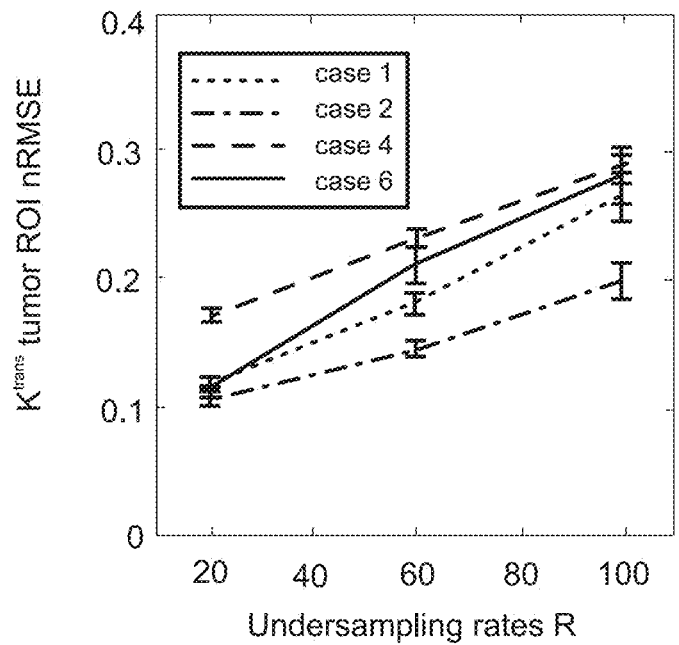
FIGS. 11A, 11B, and 11C. Quantitative evaluation of the joint AIF and TK reconstruction for four in vivo retrospectives under-sampled cases across R=20×, 60×, and 100×.
Figure 11B:
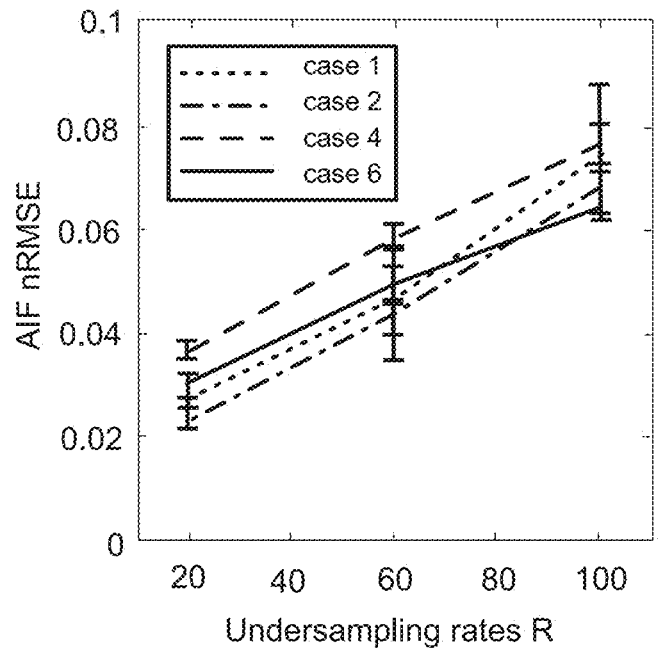
Figure 11C:
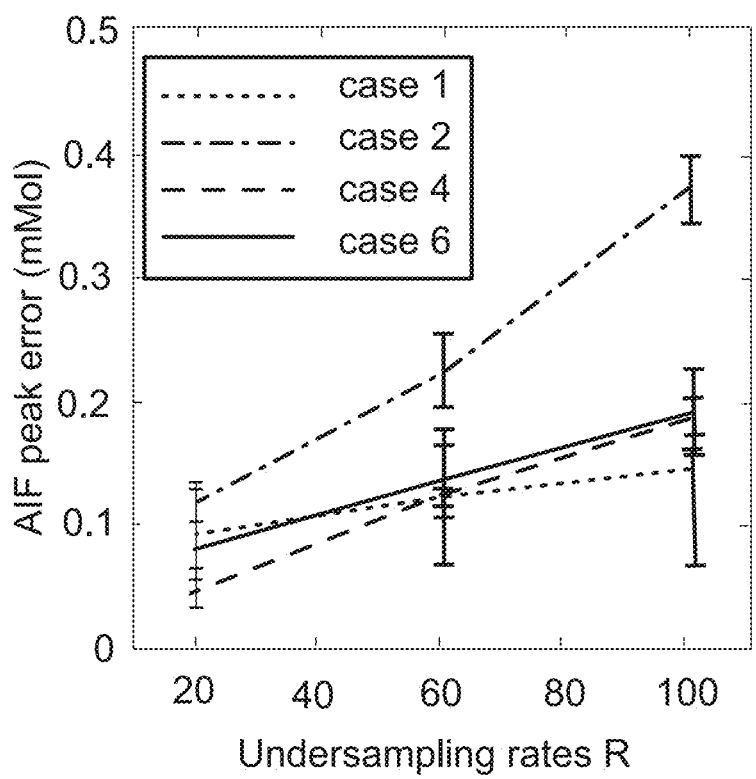

FIG. 11 shows the quantitative evaluation of joint AIF and TK reconstruction across the four in vivo data sets. Based on the nRMSE of the TK maps, TK maps can be restored with error less than 30% at for all cases and under-sampling rates. Radial sampling patterns with different initial angle created different noise realization for each case, and multiple noise realizations show that the method is robust to noise, with an expected increase in variance at higher under-sampling rates. The shape of the AIF can be estimated at up to R=100×, with AIF nRMSE below 8% for all cases. The peak of the AIF shows larger variance for different noise realization, since the peak is only one point. However, the proposed method is still able to restore the AIF peak up to R=60×, with the error at most 0.25 mmol across all cases.

Figure 12:
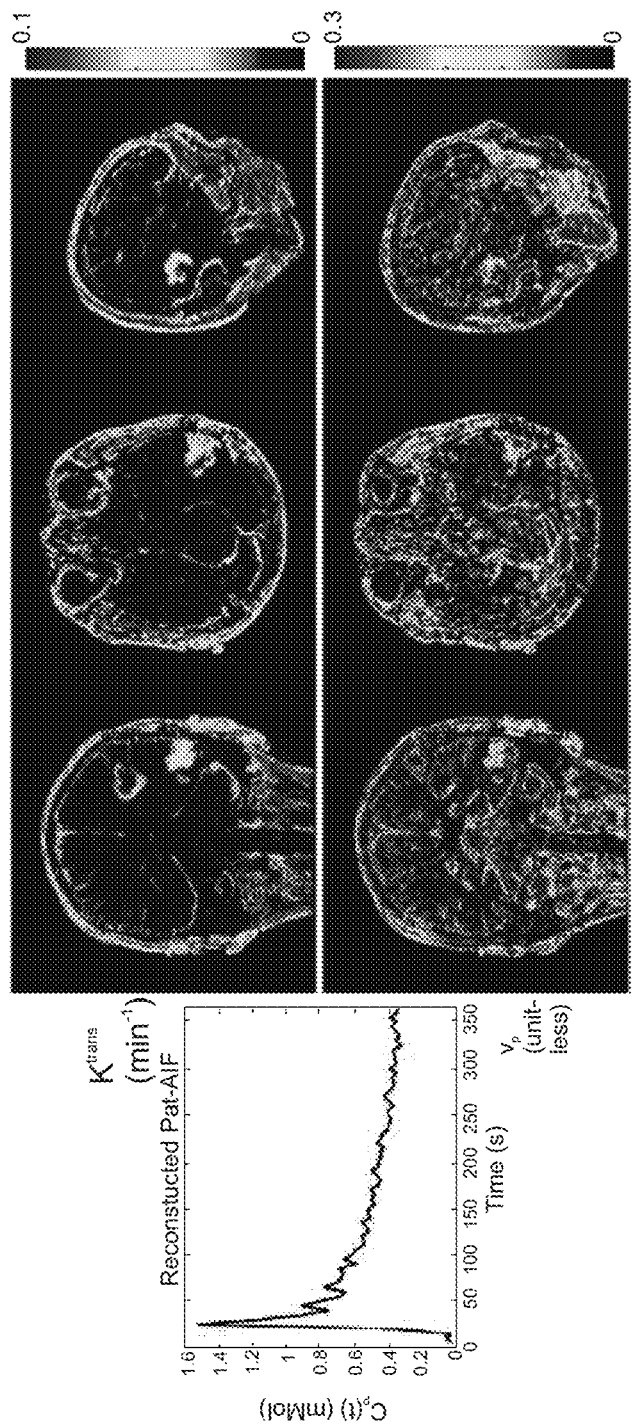
FIG. 12. Joint reconstruction of pat-AIF and TK maps from in vivo prospective under-sampled data.

FIG. 12 shows reconstruction of pat-AIF and TK maps from prospectively under-sampled in vivo data from a brain tumor patient. This result demonstrates that whole-brain TK maps can be reconstructed jointly with patient-specific AIF, with no obvious under-sampling artifacts in the final TK maps. The clinically meaningful benefits of under-sampling can be best demonstrated in a prospective study, where arbitrary reformats of the 3D TK maps are made possible by the ability to achieve high spatial resolution and whole-brain coverage.

DISCUSSION

We have described, demonstrated, and evaluated a novel model-based reconstruction approach for DCE-MRI in which the TK model is posed as a penalized consistency constraint. By this formulation, we decoupled the TK model consistency from the k,t space data consistency. The two sub-problems can be solved using existing techniques, namely TK modeling (including AIF estimation) and regularized SENSE reconstruction. The proposed approach allows for easy inclusion of different TK solvers, including third-party solvers, and also allows for joint estimation of the patient-specific AIF. We have demonstrated the robustness of the proposed method in one anatomically realistic brain tumor DRO, and a retrospective study of nine brain tumor DCE-MRI datasets. The DRO study demonstrated that the proposed method provides performance comparable to conventional TK modeling results from fully sampled noisy images, with only a 2% higher error at 60-fold under-sampling. The retrospective study shows that the proposed method is robust to noise across different cases, and can provide accurate TK maps with less than 32% error, and AIF with less than 8% error up to 100-fold under-sampling.

We also demonstrated the application of the proposed method to prospectively under-sampled data, where whole-brain high-resolution TK maps can be jointly reconstructed with pat-AIF. The proposed method has a few important limitations. First, the alternating algorithm proposed is a two-loop iteration, where an iterative solver is needed for each subproblem. Compared with a gradient-based direct reconstruction (14), this formulation takes longer computing time. This issue can be addressed by using more powerful computers, implementing in C, and/or using GPU acceleration.

Second, although we demonstrate that the proposed method is compatible with a third-party solver, it requires that the solver not use any approximation for the modeling. This is because the proposed approach requires the backward and forward modeling operators to be exact inverses of each other, otherwise error will accumulate during the iteration process. For higher-order TK models, a few linearized approximation approaches have been proposed for fast computation (46,47). Unfortunately, those approximation methods are not compatible with this framework.

Third, although we have shown that this method can include different TK solver, it may be difficult to use a nested model that selects between several different local models based on local fitting errors (23-25). This type of approach has been shown in the literature to be advantageous. The quality of intermediate anatomic images in the proposed method, especially in the first few iterations, may make it challenging to generate a modeling mask needed for nested models.

Fourth, we have not accounted for phase that can be induced by the contrast agent (primarily in vessels). Many centers, including ours, use a half dose for DCE-MRI, which makes this effect negligible. If a full dose is used, the potential phase effects on the AIF signal can and should be modeled using the closed-form solution by Simonis et al. (48).

In conclusion, we have demonstrated a novel model-based reconstruction approach for accelerated DCE-MRI. Posing the TK model as a model consistency constraint, this formulation provides flexible use of different TK solvers, joint estimation of pat-AIF, and straightforward implementation. In anatomically realistic brain tumor DRO studies, the proposed method provides TK maps with low error that are comparable to fully sampled data. In retrospective under-sampling studies, this method provides TK maps with nRMSE less than 32% and pat-AIF with nRMSE less than 8% at under-sampling rates up to 100×.

APPENDIX

The proposed method uses an alternating approach to solve for C and $\theta$ from under-sampled k,t-space data. This appendix details the steps involved in solving the two sub-problems shown in Eqn [4] and Eqn [5].

In Eqn [4], we solve for the contrast concentration vs time from the measured data using the following equation:

$$C^{n+1} = \underset{C}{\operatorname{argmin}} \|AC - b\|_2^2 + \beta \|P(\theta^n) - C\|_2^2 \qquad [3]$$

where $A=UFE\Psi$. We first solve for the image difference ($\Delta S$) from b (since the pre-contrast signal $S_0$ is included in b) by solving the following least-square problems using CG (or another iterative algorithm for least-square problems). We use the result from the previous iteration as an initial guess for faster convergence.

$$\Delta S = \underset{\Delta S}{\operatorname{argmin}} \|UFE(\Delta S) - b\|_2^2 + \|\Delta S - \psi P(\theta^n)\|_2^2 \quad [A.1]$$

where first term represents SENSE, and the second term is an identity constraint to $\Psi P(\theta'')$ that is constant in this step. P is the forward modeling from TK maps to contrast concentration vs time C, and $\Psi$ is the conversion from contrast concentration C to signal difference $\Delta S$ following the steady-state SPGR signal equation:

$$\Delta S = \psi(C) = \frac{M_0 \sin\alpha(1 - e^{-TR \cdot (R_0 + C \cdot r_1)})}{1 - \cos\alpha e^{-TR \cdot (R_0 + C \cdot r_1)}} - \frac{M_0 \sin\alpha(1 - e^{-TR \cdot R_0})}{1 - \cos\alpha e^{-TR \cdot R_0}} \quad [A.2]$$

where TR is the repetition time, a is the flip angle, $r_1$ is the contrast agent relaxivity. $R_0$ and $M_0$ are the pre-contrast $R_1$ (reciprocal of $T_1$) and the equilibrium longitudinal magnetization that are estimated from a $T_1$ mapping sequence. In this work, we used DESPOT1 (49) prior to the DCE-MRI scan.

Note that $\Psi$ is a one-to-one mapping for each voxel, and its inversion ($C = \Psi^{-1}(\Delta S)$) is:

$$R_t = -\frac{1}{TR} \ln \frac{1 - \left(\frac{\Delta S}{M_0 \sin\alpha} + \frac{1 - e^{-TR \cdot R_0}}{1 - \cos\alpha e^{-TR \cdot R_0}}\right)}{1 - \cos\alpha \left(\frac{\Delta S}{M_0 \sin\alpha} + \frac{1 - e^{-TR \cdot R_0}}{1 - \cos\alpha e^{-TR \cdot R_0}}\right)} \quad [A.3]$$

$$C = (R_t - R_0)/r_1$$

Eqn [A.3] is used to compute C after solving for $\Delta S$ using Eqn [A.1], this completes the detailed algorithm for solving Eqn [4].

After C is estimated, Eqn [5] represents backward TK modelling. C(t) is used in the equation below to avoid confusion. For the Patlak model, Eqn [4] is expressed as:

$$C(t) = P(\theta) = P(K^{trans}, v_p) = K^{trans} \int_0^t C_p(\tau) d\tau + v_p C_p(t) \quad [A.4]$$

Where $C_p(t)$ is the arterial input function (AIF). The Patlak model is linear, and a pseudo-inverse can be used to solve $\theta = P^{-1}(C)$.

For the extended-Tofts (eTofts) model, Eqn [4] is expressed as:

$$C(t) = \quad [A.5]$$
$$P(\theta) = P(K^{trans}, v_p, K_{ep}) = K^{trans} \int_0^t C_p(\tau) e^{-K_{ep}^{(t-\tau)}} d\tau + v_p C_p(t)$$

where an extra TK parameter $K_{ep}$ is modeled for better fitting. eTofts is nonlinear, and an iterative algorithm can be used to solve this model fitting:

$$\theta = \underset{\theta}{\operatorname{argmin}} \|P(\theta) - C\|_2^2 \quad [A.6]$$

We use a gradient-based 1-BFGS algorithm to solve Eqn [A.6], where we derive the gradient for each TK parameter. In this study, we also used an open-source DCE-MRI TK modeling toolbox, Rocketship (31), for comparison.

The code and examples of the proposed algorithm are publicly available at "github.com/usc-mrel/DCE_MOCCO;" the entire disclosure of which is hereby incorporated by reference.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. Heye A K, Culling R D, Hernandez C V, Thrippleton M J, Wardlaw J M. Assessment of blood-brain barrier disruption using dynamic contrast-enhanced MRI. A systematic review. Neuroimage Clin 2014; 6:262-274.

2. Tofts P S, Kermode A G. Measurement of the blood-brain barrier permeability and leakage space using dynamic MR imaging. 1. Fundamental concepts. Magn Reson Med 1991; 17:357-367.

3. O'Connor J P B, Jackson A, Parker G J M, Roberts C, Jayson G C. Dynamic contrast-enhanced MRI in clinical trials of antivascular therapies. Nat Rev Clin Oncol 2012; 9:167-177.

4. Larsson H B, Stubgaard M, Frederiksen J L, Jensen M, Henriksen O, Paulson O B. Quantitation of blood-brain barrier defect by magnetic resonance imaging and gadolinium-DTPA in patients with multiple sclerosis and brain tumors. Magn Reson Med 1990; 16:117-131.

5. Law M, Yang S, Babb J S, et al. Comparison of cerebral blood volume and vascular permeability from dynamic susceptibility contrast-enhanced perfusion MR imaging with glioma grade. Am J Neurora-diol 2004; 25:746-755.

6. Montagne A, Barnes S R, Law M, et al. Blood-brain barrier breakdown in the aging human hippocampus. Neuron 2015; 85:296-302.

7. Henderson E, Rutt B K, Lee T Y. Temporal sampling requirements for the tracer kinetics modeling of breast disease. Magn Reson Imaging 1998; 16:1057-1073.

8. Cramer S P, Simonsen H, Frederiksen J L, Rostrup E, Larsson H B W. Abnormal blood-brain barrier permeability in normal appearing white matter in multiple sclerosis investigated by MRI. Neuroimage Clin 2014; 4:182-189.

9. Guo Y, Lebel R M, Zhu Y, et al. High-resolution whole-brain DCE-MRI using constrained reconstruction: prospective clinical evaluation in brain tumor patients. Med Phys 2016; 43:2013-2023.

10. Feng L, Grimm R, Block K T, et al. Golden-angle radial sparse parallel MRI: combination of compressed sensing, parallel imaging, and golden-angle radial sampling for fast and flexible dynamic volumetric MRI. Magn Reson Med 2014; 72:707-717.

11. Lebel R M, Jones J, Ferre J-C, Law M, Nayak K S. Highly accelerated dynamic contrast enhanced imaging. Magn Reson Med 2014; 71:635-644.

12. Zhang T, Cheng J Y, Potnick A G, et al. Fast pediatric 3D free-breathing abdominal dynamic contrast enhanced MRI with high spatiotemporal resolution. J Magn Reson Imaging 2015; 41:460-473.

13. Chandarana H, Feng L, Ream J, et al. Respiratory motion-resolved compressed sensing reconstruction of free-breathing radial acquisition for dynamic liver magnetic resonance imaging. Invest Radiol 2015; 50:749-756.

14. Guo Y, Lingala S G, Zhu Y, Lebel R M, Nayak K S. Direct estimation of tracer-kinetic parameter maps from highly under sampled brain dynamic contrast enhanced MRI. Magn Reson Med 2016. doi: 10.1002/mrm.26540.

15. Sumpf T J, Uecker M, Boretius S, Frahm J. Model-based nonlinear inverse reconstruction for T2 mapping using highly under sampled spin-echo MRI. J Magn Reson Imaging 2011; 34:420-428.

16. Velikina J V, Alexander A L, Samsonov A. Accelerating MR parameter mapping using sparsity-promoting regularization in parametric dimension. Magn Reson Med 2013; 70:1263-1273.

17. Lin Y, Haldar J, Li Q, Conti P, Leahy R. Sparsity constrained mixture modeling for the estimation of kinetic parameters in dynamic PET. IEEE Trans Med Imaging 2013; 33:173-185.

18. Wang G, Qi J. Direct estimation of kinetic parametric images for dynamic PET. Theranostics 2013:802-815.

19. Dikaios N, Arridge S, Hamy V, Punwani S, Atkinson D. Direct parametric reconstruction from under sampled (k, t)-space data in dynamic contrast enhanced MRI. Med Image Anal 2014; 18:989-1001.

20. Felsted B K, Whitaker R T, Schabel M, DiBella E V R. Model-based reconstruction for under sampled dynamic contrast-enhanced MRI. Proc SPIE 2009; 7262:1-10.

21. Lingala S G, Guo Y, Zhu Y, Barnes S, Lebel R M, Nayak K S. Accelerated DCE MRI Using Constrained Reconstruction Based on Pharmaco-kinetic Model Dictionaries. In Proceedings of the 23rd Annual Meeting of ISMRM, Toronto, Ontario, Canada, 2015. p. 196.

22. Port R E, Knopp M V, Brix G. Dynamic contrast-enhanced MRI using Gd-DTPA: interindividual variability of the arterial input function and consequences for the assessment of kinetics in tumors. Magn Reson Med 2001; 45:1030-1038.

23. Ewing J R, Brown S L, Lu M, et al. Model selection in magnetic resonance imaging measurements of vascular permeability: gadomer in a 9L model of rat cerebral tumor. J Cereb Blood Flow Metab 2006; 26: 310-320.

24. Bagher-ebadian H, Jain R, Nejad-davarani S P, et al. Model selection for DCE-T1 studies in glioblastoma. Magn Reson Med 2012:241-251.

25. Ewing J R, Bagher-Ebadian H. Model selection in measures of vascular parameters using dynamic contrast-enhanced MRI: experimental and clinical applications. NMR Biomed 2013:1028-1041.

26. Shi L, Wang D, Liu W, et al. Automatic detection of arterial input function in dynamic contrast enhanced MRI based on affinity propagation clustering. J Magn Reson Imaging 2014:1327-1337.

27. Parker G J M, Roberts C, Macdonald A, et al. Experimentally-derived functional form for a population-averaged high-temporal-resolution arterial input function for dynamic contrast-enhanced MRI. Magn Reson Med 2006; 56:993-1000.

28. Samsonov A. A Novel Reconstruction Approach Using Model Consistency Condition for Accelerated Quantitative MRI (MOCCA). In Proceedings of the 20th Annual Meeting of ISMRM, Melbourne, Victoria, Australia, 2012. p. 358.

29. Velikina J V, Samsonov A A. Reconstruction of dynamic image series from under sampled MRI data using data-driven model consistency condition (MOCCO). Magn Reson Med 2015; 74:1279-1290.

30. Pruessmann K P, Weiger M, Bo€rnert P, Boesiger P. Advances in sensi-tivity encoding with arbitrary k-space trajectories. Magn Reson Med 2001; 46:638-651.

31. Barnes S R, Ng T S C, Santa-Maria N, Montagne A, Zlokovic B V, Jacobs R E. ROCKETSHIP: a flexible and modular software tool for the planning, processing and analysis of dynamic MRI studies. BMC Med Imaging 2015; 15:19.

32. Barboriak D P, MacFall J R, Padua A O, York G E, Viglianti B L and M W D. Standardized Software for Calculation of Ktrans and vp from Dynamic T1-Weighted MR Images. Presented at the ISMRM Workshop on MR in Drug Development: From Discovery to Clinical Therapeutic Trials, McLean, Virginia, USA, April 2004.

33. Dikaios N, Punwani S, Atkinson D. Direct Parametric Reconstruction from (k, t)-Space Data in Dynamic Contrast Enhanced MRI. In Proceedings of the 23rd Annual Meeting of ISMRM, Toronto, Ontario, Canada, 2015. p. 3706.

34. Bosca R J, Jackson E F. Creating an anthropomorphic digital MR phantom—an extensible tool for comparing and evaluating quantitative imaging algorithms. Phys Med Biol 2016; 61:974-982.

35. Zhu Y, Guo Y, Lingala S G, et al. Evaluation of DCE-MRI Data Sampling, Reconstruction and Model Fitting Using Digital Brain Phantom. In Proceedings of the 23rd Annual Meeting of ISMRM, Toronto, Ontario, Canada, 2015. p. 3070.

36. Stanisz G J, Henkelman R M. Gd-DTPA relaxivity depends on macro-molecular content. Magn Reson Med 2000; 44:665-667.

37. Zhu Y, Guo Y, Lingala S G, Lebel R M, Law M, Nayak K S. GOCART: GOlden-angle CArtesian randomized time-resolved 3D MRI. Magn Reson Imaging 2016; 34:940-950.

38. Thomas A A, Arevalo-Perez J, Kaley T, et al. Dynamic contrast enhanced T1 MRI perfusion differentiates pseudo-progression from recurrent glioblastoma. J Neurooncol 2015; 125:183-190.

39. Jung S C, Yeom J A, Kim J, et al. Glioma: application of histogram analysis of pharmacokinetic parameters from T1-weighted dynamic contrast-enhanced MR imaging to tumor grading. AJNR Am J Neuro-radiol 2014:1103-1110.

40. Markowski C A, Markowski E P. Conditions for the effectiveness of a preliminary test of variance. Am Stat 1990; 44:322-326.

41. Anderson K B, Conder J A. Discussion of multicyclic Hubbert modeling as a method for forecasting future petroleum production. Energy Fuels 2011; 25:1578-1584.

42. Lebel R M, Guo Y, Zhu Y, et al. The Comprehensive Contrast-Enhanced Neuro Exam. In Proceedings of the 23rd Annual Meeting of ISMRM, Toronto, Ontario, Canada, 2015. p. 3705.

43. Baek H J, Kim H S, Kim N, Choi Y J, Kim Y J. Percent change of perfusion skewness and kurtosis: a potential imaging biomarker for early treatment response in patients with newly diagnosed glioblastomas. Radiology 2012; 264:834-843.

44. Guo Y, Lebel R M, Zhu Y, et al. High-Resolution Whole-Brain DCE-MRI Using constrained reconstruction: prospective clinical evaluation in brain tumor patients. Med Phys 2016; 43:2013.

45. Bertsekas D P. Multiplier methods: a survey. Automatica 1976; 12:133-145.

46. Murase K. Efficient method for calculating kinetic parameters using T1-weighted dynamic contrast-enhanced magnetic resonance imaging. Magn Reson Med 2004;51: 858-862.

47. Flouri D, Lesnic D, Sourbron S P. Fitting the two-compartment model in DCE-MRI by linear inversion. Magn Reson Med 2016; 76:998-1006.

48. Simonis F F, Sbrizzi A, Beld E, Lagendijk J J, van den Berg C A. Improving the arterial input function in dynamic contrast enhanced MRI by fitting the signal in the complex plane. Magn Reson Med 2016; 76:1236-1245.

49. Deoni S C L, Peters T M, Rutt B K. High-resolution T1 and T2 mapping of the brain in a clinically acceptable time with DESPOT1 and DES-POT2. Magn Reson Med 2005; 53:237-241.

What is claimed is:

1. A method for improving dynamic contrast enhanced imaging for joint arterial input function and tracer kinetic parameter estimation, the method comprising:
   a) administering a contrast agent to a subject;
   b) collecting imaging data from the subject for a tissue or organ;
   c) selecting a tracer kinetic model to be applied to the imaging data, the tracer kinetic model being defined by a plurality of tracer kinetic parameters;
   d) reconstructing dynamic images from the imaging data as reconstructed dynamic images, wherein a consistency constraint is applied to the reconstructed dynamic images; the consistency constraint including a weighted sum of a data consistency component and a model consistency component;
   e) applying the tracer kinetic model to the reconstructed dynamic images to estimate tracer kinetic parameter maps as estimated tracer kinetic parameter maps wherein a model consistency restraint is applied; and
   f) alternately performing steps d) and e) until converging on a set of dynamic images and tracer kinetic parameter maps, wherein the consistency constraint is estimated by a least square optimization formulated as:

$$(C, \theta) = \underset{C, \theta}{\operatorname{argmin}} \|UFE(\psi C + S_0) - y\|_2^2 + \beta \|P(\theta) - C\|_2^2$$

$\Psi$ is a signal operator which converts concentration-time-curves (per voxel) C of the contrast agent to an image intensity time series;
U is an under-sampling mask;
F is a Fourier transform;
E is a sensitivity encoding matrix providing spatial relative sensitivities of pickup coils;
$S_0$ is image intensity for each voxel prior to contrast agent arrival;
y is under-sampled magnetic resonance imaging data:
C is a measured concentration-time curves of the contrast agent for each voxel in a Field Of View;
$P(\theta)$ is a predicted concentration distribution of the contrast agent from a selected tracer kinetic model;
$\beta$ is a penalty or weight factor for the model consistency component; and
$\theta$ are tracer kinetic parameters.

2. The method of claim 1 wherein the tracer kinetic model is selected from a library of tracer kinetic models such that one or more tracer kinetic model from the library are applied to find an optimal tracer kinetic model.

3. The method of claim 1 wherein the imaging data is magnetic resonance imaging data.

4. The method of claim 1 wherein the imaging data is dynamic contrast positron emission tomography data.

5. The method of claim 1 wherein the data consistency component being enforced before the model consistency component.

6. The method of claim 1 further determining at least one of an arterial input function or vascular input function from the imaging data, wherein the arterial input function includes a time variation of contrast agent concentration at one or more predetermined locations in an artery of the subject.

7. The method of claim 6 wherein the arterial input function is smoothed or forced to a model.

8. The method of claim 6 wherein the arterial input function is taken as surrogate for the vascular input function.

9. The method of claim 6 wherein the arterial input function is determined as a function of time.

10. The method of claim 1 wherein the tissue or organ is selected from the group consisting of brain, breast, prostate, liver, kidney, lung, heart, thyroid, pancreas, spleen, intestine, uterus, ovary, limbs, spine, bones, and eyes.

11. The method of claim 1 further comprises automatically selecting reference tissue and vessels for arterial input functions (AIF) extraction in each iteration based on a current image series.

12. The method of claim 11 wherein reference tissue and vessels for AIF extraction are automatically selected from voxels of relative or absolute peak enhancement or by comparison to a population based reference AIF, or by model order estimation methods.

13. The method of claim 1 wherein the tracer kinetic model is automatically identified and selected.

14. The method of claim 13 wherein the tracer kinetic model is automatically selected by specifying a collection of possible models, inclusive of nested or not nested models, from which a model identification method is applied to select a model for each voxel or region.

15. The method of claim 1 wherein the tracer kinetic parameter maps and the dynamic images are simultaneously reconstructed.

16. The method of claim 1 wherein the tracer kinetic model is a Patlak model.

17. The method of claim 1 wherein the tracer kinetic model is an extended Tofts model.

18. The method of claim 1, wherein selecting the tracer kinetic model includes jointly estimating contrast concentration versus time images and TK parameter maps from under-sampled (k,t) space data.

19. The method of claim 1 wherein the tracer kinetic model is a Patlak model and $\theta$ includes $K^{trans}$ and $v_p$ where $K^{trans}$ is a transfer constant from blood plasma into extracellular extravascular space (EES) and $v_p$ is fractional plasma volume.

20. The method of claim 1 wherein the tracer kinetic model is an extended Tofts model and $\theta$ includes $v_p$, $K^{ep}$ and $v_e$ where Ktrans is a transfer constant from blood plasma into extracellular extravascular space (EES), $v_p$ is fractional plasma volume, $K^{ep}$ is a transfer constant from EES back to the blood plasma, and $v_e$ is a fractional EES volume.

21. The method of claim 1 wherein all steps are repeated for multiple slices through the subject being imaged and three-dimensional image data are reconstructed.

22. A system for improving dynamic contrast enhanced imaging for joint arterial input function and tracer kinetic parameter estimation, the system comprising:

a magnetic resonance imaging system that generates magnetic resonance imaging data from a subject for a tissue or organ; and a programmable computer configured to execute steps of:
a) collecting the magnetic resonance imaging data from the subject;
b) reconstructing dynamic images from the magnetic resonance imaging data as reconstructed dynamic images, wherein a consistency constraint is applied to the reconstructed dynamic images; the consistency constraint including a weighted sum of a data consistency component and a model consistency component;
c) applying a tracer kinetic model to the reconstructed dynamic images to estimate tracer kinetic parameter maps as estimated tracer kinetic parameter maps, wherein a model consistency constraint is applied; and
d) alternately performing steps b) and c) until converging on a set of dynamic images and tracer kinetic parameter maps, wherein the consistency constraint is estimated by a least square optimization formulated as:

$$(C, \theta) = \underset{C,\theta}{\mathrm{argmin}} \|UFE(\psi C + S_0) - y\|_2^2 + \beta \|P(\theta) - C\|_2^2$$

$\Psi$ is a signal operator which converts concentration-time-curves (per voxel) C of a contrast agent to an image intensity time series;
U is an under-sampling mask;
F is a Fourier transform;
E is a sensitivity encoding matrix providing spatial relative sensitivities of pickup coils;
$S_0$ is image intensity for each voxel prior to contrast agent arrival;
y is under-sampled magnetic resonance imaging data:
C is a measured concentration-time curves of the contrast agent for each voxel in a Field Of View;
$P(\theta)$ is a predicted concentration distribution of the contrast agent from a selected tracer kinetic model;
$\beta$ is a penalty or weight factor for the model consistency component; and
$\theta$ are tracer kinetic parameters.

23. The system of claim 22 wherein steps a through d are repeated for multiple slices through the subject and three-dimensional image data are reconstructed.

24. The system of claim 22 wherein the programmable computer is further operable to select the tracer kinetic model to be applied to the magnetic resonance imaging data, the tracer kinetic model being defined by plurality of tracer kinetic parameters.

25. The system of claim 22 wherein the programmable computer applies the data consistency component before the model consistency component.

26. The system of claim 22 wherein the programmable computer is operable to determine an arterial input function or vascular input function from the magnetic resonance imaging data, wherein the arterial input function includes a time variation of the contrast agent at one or more predetermined locations in an artery of the subject.

27. The system of claim 26 wherein the arterial input function is taken as surrogate for the vascular input function.

28. The system of claim 26 wherein the arterial input function is determined as a function of time.

29. The system of claim 26 wherein reference tissue and vessels for AIF extraction are automatically selected in each iteration based on a current image series.

30. The system of claim 29 further comprises autocratically selecting reference tissue and vessels for arterial input functions (AIF) extraction from voxels of relative or absolute peak enhancement or by comparison to reference (population based) AIF or by a model order estimation method.

31. The system of claim 22 wherein the programmable computer is operable to identify and select the tracer kinetic model from a library of tracer kinetic models.

32. The system of claim 22 wherein the programmable computer is operable to automatically select the tracer kinetic model by specifying a collection of possible models (nested or not nested) from which a model identification method is applied to select a model for each voxel or region.

33. The system of claim 22 wherein the tracer kinetic parameter maps and the dynamic images are simultaneously reconstructed.

34. The system of claim 22 wherein the tracer kinetic model is a Patlak model or an extended Tofts model.

* * * * *